United States Patent
Kikuchi et al.

(10) Patent No.: US 12,071,624 B2
(45) Date of Patent: Aug. 27, 2024

(54) ANTISENSE OLIGONUCLEOTIDE TARGETING ARL4C MOLECULE, AND NUCLEIC ACID DRUG USING ANTISENSE OLIGONUCLEOTIDE

(71) Applicants: OSAKA UNIVERSITY, Suita (JP); NATIONAL INSTITUTES OF BIOMEDICAL INNOVATION, HEALTH AND NUTRITION, Ibaraki (JP); NATIONAL UNIVERSITY CORPORATION KOBE UNIVERSITY, Kobe (JP)

(72) Inventors: Akira Kikuchi, Suita (JP); Shinji Matsumoto, Suita (JP); Satoshi Obika, Ibaraki (JP); Yuya Kasahara, Ibaraki (JP); Takumi Fukumoto, Kobe (JP)

(73) Assignees: Osaka University, Osaka (JP); National Institutes of Biomedical Innovation, Health and Nutrition, Osaka (JP); National University Corporation Kobe University, Hyogo (JP)

( * ) Notice: Subject to any disclaimer, the term of this patent is extended or adjusted under 35 U.S.C. 154(b) by 452 days.

(21) Appl. No.: 17/250,806

(22) PCT Filed: Sep. 4, 2019

(86) PCT No.: PCT/JP2019/034746
§ 371 (c)(1),
(2) Date: Mar. 4, 2021

(87) PCT Pub. No.: WO2020/050307
PCT Pub. Date: Mar. 12, 2020

(65) Prior Publication Data
US 2021/0317459 A1      Oct. 14, 2021

(30) Foreign Application Priority Data

Sep. 5, 2018 (JP) ................................. 2018-165544

(51) Int. Cl.
| | |
|---|---|
| *C07H 21/04* | (2006.01) |
| *A61P 35/04* | (2006.01) |
| *C12N 15/113* | (2010.01) |

(52) U.S. Cl.
CPC .......... *C12N 15/1137* (2013.01); *A61P 35/04* (2018.01); *C12N 2310/11* (2013.01); *C12N 2310/315* (2013.01)

(58) Field of Classification Search
CPC ............ C12N 15/1137; C12N 2310/11; C12N 2310/315; A61P 35/04
See application file for complete search history.

(56) References Cited

U.S. PATENT DOCUMENTS

2014/0154783 A1* 6/2014 Rossomando ....... C12N 15/113
                                                         435/239
2018/0105881 A1   4/2018 Piquemal

FOREIGN PATENT DOCUMENTS

JP    2015-231978 A    12/2015
WO   WO 2016/027029 A2   2/2016

OTHER PUBLICATIONS

Gavrilov K, Saltzman WM. Therapeutic siRNA: principles, challenges, and strategies. Yale J Biol Med. Jun. 2012;85(2):187-200 . . . PMID: 22737048; PMCID: PMC3375670. (Year: 2012).*
"Arl4c expression in colorectal and lung cancers promotes tumorigenesis and may represent a novel therapeutic target". S Fujii, S Matsumoto, S Nojima, E Morii and A Kikuchi. Oncogene, 34, 4834-4844. (Year: 2015).*
Fakhr E, Zare F, Teimoori-Toolabi L. Precise and efficient siRNA design: a key point in competent gene silencing. Cancer Gene Ther.; 23(4):73-82. doi: 10.1038/cgt.2016.4. PMID: 26987292. (Year: 2016).*
Li et al. "ATF3 demethylation promotes the transcription of ARL4C, which acts as a tumor suppressor in human breast cancer." OncoTargets and therapy (2020): 3467-3476.*
Yamamoto, Tsuyoshi, et al. ("Amido-bridged nucleic acids with small hydrophobic residues enhance hepatic tropism of antisense oligonucleotides in vivo." Organic & biomolecular chemistry 13.12 (2015): 3757-3765).*
Extended European Search Report in Counterpart European Patent Application No. 19856678.8 dated Jan. 4, 2023.
Hu, Q. et al., "Identification of ARL4C as a Peritoneal Dissemination-Associated Gene and Its Clinical Significance in Gastric Cancer", *Ann. Surg. Oncol.* (2018) 25:745-753.
Yamauchi, J. et al., "Valproic acid-inducible ARI4D and cytohesin-2/ARNO, acting through the downstream Arf6, regulate neurite outgrowth in N1E-115 cells", *Experimental Cell Research* (2009) 315:2043-2052.
International Search Report of PCT/JP2019/034746 mailed Nov. 26, 2019.
Matsumoto S. et al., "Arl4c is a key regulator of tubulogenesis and tumourigenesis as a target gene of Wnt-β-catenin and growth factor-Ras signalling". J Biochem 2017; 161: 27-35.

(Continued)

*Primary Examiner* — Kimberly Chong
(74) *Attorney, Agent, or Firm* — Knobbe, Martens, Olson & Bear, LLP

(57) ABSTRACT

The purpose of the present invention is to provide an antisense oligonucleotide that targets an ARL4C molecule and exerts an antitumor effect in vivo, and a nucleic acid drug using the antisense oligonucleotide. An antisense oligonucleotide that has a base sequence consisting of at least 10 consecutive bases contained in the base sequence represented by SEQ ID NO: 1. This antisense oligonucleotide targets an ARL4C molecule and thus can inhibit the expression of ARL4C in a tumor cell in vitro and suppress the migration and proliferation thereof. When systemically administered, moreover, the antisense oligonucleotide can exert an excellent antitumor effect in vivo too.

13 Claims, 12 Drawing Sheets

Specification includes a Sequence Listing.

(56) References Cited

OTHER PUBLICATIONS

D'Souza-Schorey C et al., "ARF proteins: roles in membrane traffic and beyond". Nat Rev Mol Cell Biol 2006; 7: 347-358.

Burd CG et al., "Arf-like GTPases: not so Arf-like after all". Trends Cell Biol 2004; 14: 687-694.

Matsumoto S. et al., "A combination of Wnt and growth factor signaling induces Arl4c expression to form epithelial tubular structures". EMBO J 2014; 33: 702-718.

Fujii S. et al., "Arl4c expression in colorectal and lung cancers promotes tumorigenesis and may represent a novel therapeutic target". Oncogene 2015; 34: 4834-4844.

Fujii S. et al., "Epigenetic upregulation of ARL4C, due to DNA hypomethylation in the 3'-untranslated region, promotes tumorigenesis of lung squamous cell carcinoma." Oncotarget 2016; vol. 7 (No. 49) 81571-81587.

Stein CA., et al., FDA-Approved Oligonucleotide Therapies in 2017. Molecular Therapy, 2017; 25: 1069-1075.

Yahara A., et al., "Amido-bridged nucleic acids (AmNAs): synthesis, duplex stability, nuclease resistance, and in vitro antisense potency". ChemBioChem 2012; 13: 2513-2516.

Bo, Xiaochen et al., "Selection of Antisense oligonucleotides based on multiple predicted target mRNA structures", BMS Bioinformatics, Mar. 9, 2006, vol. 7, 122 (pp. 1-12).

Harada, Takeshi et al., "Chemically Modified Antisense Oligonucleotide Against ARL4C Inhibits Primary and Metastatic Liver Tumor Growth", Molecular Cancer Therapeutics, Jan. 15, 2019, vol. 18, No. 3, pp. 602-612.

* cited by examiner

SEQUENCE LISTING

```
<160> NUMBER OF SEQ ID NOS: 105

<210> SEQ ID NO 1
<211> LENGTH: 15
<212> TYPE: DNA
<213> ORGANISM: Artificial Sequence
<220> FEATURE:
<223> OTHER INFORMATION: Antisense nucleotide targeting ARL4C

<400> SEQUENCE: 1
gcatacctca ggtaa                                                      15

<210> SEQ ID NO 2
<211> LENGTH: 19
<212> TYPE: DNA
<213> ORGANISM: Artificial Sequence
<220> FEATURE:
<223> OTHER INFORMATION: Antisense nucleotide targeting ARL4C

<400> SEQUENCE: 2
gcatacctca ggtaattca                                                  19

<210> SEQ ID NO 3
<211> LENGTH: 3838
<212> TYPE: RNA
<213> ORGANISM: Homo sapiens

<400> SEQUENCE: 3
gacugugagg cugccgagcg dacagcgacu cccgggaag cccgcgcucc gggagcggga    60
```

-continued

| | |
|---|---|
| gcgggagcag gagcaggagc agcgccgucc caggccagag gcgagcgccg ggcgccggga | 120 |
| gagcggagag cccgggcagc ugccggagcg cgggggcgcg gcccgaggaa accacagagc | 180 |
| gagcccaggc cuggggaggg cgccgaacau cugaggcggc uucgcgggag acaaagccgc | 240 |
| gcguagagac gcgaugcccg ccgaucgcga gcccggccgg cgaggcgcg gggacugcgg | 300 |
| cgucugagcg cgccaagccg ugcgcccgcg gggacgccga gccccggggc cggugcgggc | 360 |
| ggcggcgggc ggggcccagg ugcgcccggc cgcgucgggc ccgugacugc cgggggggcg | 420 |
| gcgcccuccc gccgcagccg caguggcugg cgccgcagcc aggagccaug ggcaacaucu | 480 |
| ccucuaacau cucggccuuc cagucccugc auaucgucau guugggcuug gacucggccg | 540 |
| gcaagaccac ggugcucuac cggcucaagu caacgaguu cgugaacacg gugcccacca | 600 |
| ucggcuucaa caccgagaag aucaagcuga gcaacggcac ggccaagggc aucagcugcc | 660 |
| acuucuggga cguggcggc caggagaagc ugcggccgcu uggaaguccc acagccgcu | 720 |
| gcacggacgg caucaucuac guggugacu cgguggacgu ggaccggcug gaggaggcca | 780 |
| agacggagcu gcacaaggug accaaguucg ccgagaacca gggcacgccg cugcugguca | 840 |
| ucgccaacaa gcaggaccug cccaagucgc ugccgguggc agagauugag aagcagcugg | 900 |
| cgcugcacga gcuuaucccg gccaccaccu aucacgucca gccggcgugc gccaucaucg | 960 |
| gcgagggccu caccgagggc auggacaagc ucuaugagau gauccugaaa cgcaggaagu | 1020 |
| cccucaagca gaagaagaag cggacugguu acuuaaggag cugcgaaguc ugauuuaccg | 1080 |
| gccuacucuc gaccugcccc ccaccccag cucaggggac cuuugucug aacgccagag | 1140 |
| cuacugacca ggucgggggg ccgcgguggg gaguggaaga gccggccug cuguccgccc | 1200 |
| ucccagcccc aggggaagg cucaguuguc ggaaagacaa aagcgauuuc uucccacucc | 1260 |
| ugcagggcca gaaguucagg cugccccgcc uccacggggg gaucgcaccu gugaauuacc | 1320 |
| ugagguaugc auuucccaga accgugggcg uaccaccuu gggggcaug uugguucugg | 1380 |
| ggggaccacc ucccuugca uucaggggcu gugaagcuga guaauuucg gucacagggc | 1440 |
| aggccccugu ugaaauuuca uuugccugc ucugggccca aggugggg uggguugggu | 1500 |
| caucagagga cugccuggga cgguucagcg ggcacggagc gcugcucugg ccuggcuggg | 1560 |
| gauggccgcg gaggugcccu uuuccugguu cuuugugguu gcugcagaag accaguuuug | 1620 |
| uugagaacug cuuuucagcc uggaaucaga caucuuccag augguuugga cccuguccau | 1680 |
| guguagguca uuaucacaca aagagaccaa uaaaaauaaa aaaauaaaaa aaaaaaag | 1740 |
| acgaacuauu ggaggugguug gccaaugaug cauuuacugu uugcaggaua guuaagguug | 1800 |
| uuuaagggu aaggcuuuug uguaaaugc uggauggggu gugugugugu guggauauag | 1860 |
| ggaccucccu cuguacugug uacuguguaa ucggcauuaa uaccuagacu cauauguauu | 1920 |
| gaauuuuaaa uucucuuagc cuacugauuu guuuggauga gcacaccagc ugcaggugug | 1980 |
| ugcugaauug caagauggua uuuuuuuuuu uaaccaaggg augucucuug uaauacuaac | 2040 |
| cgcgugauaa uggguuuuca gacaugauga aaaaaaaaa cuuuuacaaa ugaauacuua | 2100 |
| ccuuagaaau auucaccuua ggaaaaaaga cuuugcucug cccuuuuaua uuccuuuaug | 2160 |
| cugcaagugg ugacauguuc agauuucuaa uuuggguucau uguggccuau cgguuuaag | 2220 |
| ucuuucauua aaaaugucuc guuagaguau uugaugucau gcaccaaaaa aauaaaaccc | 2280 |
| caccuuguug caaaagcuga ccucguugca uggaauuaaa agagaaggaa aaacacaagg | 2340 |
| augaagucuu uccgaauuca uucuuguggg aacuggccuu cggagccagc cagcacuuug | 2400 |
| ggcaaaugca aacaacaaug agugcuugag auaaaagaaa gugugacguc auggucacug | 2460 |

```
guacucaggc acuucacagu uuacuugaaa gaggcuuugg aaaauagaua aagugaaaga   2520
agaauaaaua cauauuuuua auaaugaauu uuuaaaaauc cuuuauaauc aggacugagu   2580
cuugguuugc agaagcuguc acuuacccug aaacacagua ucaaaaggga aacuuaaaac   2640
auacuguuug auuuuuuuau uccucuuac aauccauguu ucagguaga auuaugacuu    2700 uccccccauu guuacacauu ucuuuacaaa ggaggccugu agaaauugga cacgaucaug   2760
cuugagcaug ugaguuaguc aaauuaugag ucccugccua uuguccauua cacaccgaau   2820
guuaauuuaa gaaccagagg cagaaguucu ggcuuccugc uugaaaccca auucuuauau   2880
gaaauuuuuu aaaagcagaa accagcagc ccaucugcuu uuucucuuuu ucgugugau    2940 uugguacccc uccaaugcug gucuuuuugu agaaacucag uagagaaagu cuagcuaagc   3000
aguguugaaa agccugcaag auuucaguuu acauaucgac agcauaucca cugauuucua   3060
aaugggcugg ucccaucauc ugaagauucu guauagaauu auuaaaaaaa aauccaucu    3120 uucuuuauuu ucuucacaug cgacaauuuc uuaagcacuu ugacauuuug guaguccac    3180 acauugaga gaauaauaua uuuauuugu gacauugcag augccaaaua cuguaaccuu    3240
cucaugauaa caauacuuag guucaagauc acuguucaaa cccugucaug cuuuaaaacu   3300
gaugcgagau gauuuuguuu uuugcauaau caauacuuaa gggugcaauc aacguuagu    3360 aaugugcag uaaaguaaag cccguggug uacaacuac uaguuaagag ucucaguuga    3420
uuucuguaau guuugaccua auaauagccc guuucgucuc ugacccaaca gaggaagcac   3480
agaucaaauc accuuggagu ggucaccagg gggacaggga gcccccccacc aauguaucaa   3540 ugggugauuu augaugccuu cugcccuuug gcgagugaau ggguuuccca uaggggaagu   3600
uggccucccu ccgugagcuu uggaaaugu uucuaauaga cacagggagg ccaguucugu    3660
uucagagcaa uuaucuuccc aaauucucug uucggugugu ggaacugugu gcccugguuu   3720
cuguuuuccu uucuacugcu guaauucucu gucucaucau ccuucucuuu uguuuccaua   3780
gccuuuuaua augcauauau gaugcuguga acagaaauaa auuauuuaua caaucaaa    3838
```

<210> SEQ ID NO 4
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-bridged nucleotide in which R is a methyl group)
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (4)..(4)
<223> OTHER INFORMATION: n is Adenine having a structure of AmNA (2',4'-bridged nucleotide in which R is a methyl group)
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (7)..(7)
<223> OTHER INFORMATION: n is Guanine having a structure of AmNA (2',4'-bridged nucleotide in which R is a methyl group)
<220> FEATURE:
<221> NAME/KEY: misc_feature

```
<222> LOCATION: (7)..(7)
<223> OTHER INFORMATION: n is a, c, g, or t
<220> FEATURE:
<221> NAME/KEY: modified_base
<222> LOCATION: (10)..(10)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(13)
<223> OTHER INFORMATION: n is a, c, g, or t

<400> SEQUENCE: 4
nagngantan ccntc                                                      15

<210> SEQ ID NO 5
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 5
nnnagcctca canncc                                                     15

<210> SEQ ID NO 6
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
```

```
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)

<400> SEQUENCE: 6
nnntctggcc tgnna                                                       15

<210> SEQ ID NO 7
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 7
```
nnnagaggag atnnt                                                       15

<210> SEQ ID NO 8
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 8
nnntggcagc tgnng                                                       15

<210> SEQ ID NO 9
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:

```
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)

<400> SEQUENCE: 9
nnntggtcac ctnnt                                                      15

<210> SEQ ID NO 10
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 10
nnntcataga gcnng                                                      15

<210> SEQ ID NO 11
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
```

```
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 11
nnnaaatcag acnnc                                                    15

<210> SEQ ID NO 12
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 12
nnngtgggaa gannt                                                    15

<210> SEQ ID NO 13
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
```

```
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 13
nnntacctca ggnna                                                      15

<210> SEQ ID NO 14
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 14
nnnacaaatg aannt                                                      15
```

<210> SEQ ID NO 15
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-bridged nucleotide in which R is a methyl group)

<400> SEQUENCE: 15 nnntttta tt ttnnt                        15

<210> SEQ ID NO 16
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of AmNA (2',4'-bridged nucleotide in which R is a methyl group)
<220> FEATURE:
<221> NAME/KEY: misc_feature -continued

```
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 16
nnngcattta canna                                                          15

<210> SEQ ID NO 17
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 17
nnnattcagc acnna                                                          15

<210> SEQ ID NO 18
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
```

```
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 18
nnncatgtct ganna                                                15

<210> SEQ ID NO 19
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 19
nnntcatttg tanna                                                15

<210> SEQ ID NO 20
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of
```

```
         AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 20
nnnaaaggaa tanna                                                    15

<210> SEQ ID NO 21
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 21
nnnttaatga aannc                                                    15
```

```
<210> SEQ ID NO 22
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)

<400> SEQUENCE: 22
nnnttatttt ttnng                                                    15

<210> SEQ ID NO 23
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
```

<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 23
nnntctcttt tannt                                                            15

<210> SEQ ID NO 24
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 24
nnnagtacca gtnnc                                                            15

<210> SEQ ID NO 25
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base

```
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 25
nnnataaagg atnnt                                                      15

<210> SEQ ID NO 26
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 26
nnntaaagaa atnng                                                      15

<210> SEQ ID NO 27
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
```

```
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 27
nnnatttgac tannt                                                     15

<210> SEQ ID NO 28
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 28
nnngactcat aannt                                                     15
```

```
<210> SEQ ID NO 29
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 29
nnnagcagga agnna                                                  15

<210> SEQ ID NO 30
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
```

```
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 30
nnngtaccaa atnna                                                    15

<210> SEQ ID NO 31
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 31
nnnactgagt ttnna                                                    15

<210> SEQ ID NO 32
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
```

<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)

<400> SEQUENCE: 32
nnncagatga tgnna                                                      15

<210> SEQ ID NO 33
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 33
nnnggatttt ttnnt                                                      15

<210> SEQ ID NO 34
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:

```
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 34
nnntattatt ctnnc                                                    15

<210> SEQ ID NO 35
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 35
nnnttacagt atnng                                                    15

<210> SEQ ID NO 36
```

```
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 36
nnngtattgt tanna                                                    15

<210> SEQ ID NO 37
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
```

<221> NAME/KEY: modified_base
<222> LOCATION: (14)..(14)
<223> OTHER INFORMATION: n is Thymine having a structure of AmNA (2',4'-
     bridged nucleotide in which R is a methyl group)

<400> SEQUENCE: 37 nnnccttaa gtnnt                                                       15

<210> SEQ ID NO 38
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
     bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
     bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
     AmNA (2',4'-bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
     AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
     bridged nucleotide in which R is a methyl group)

<400> SEQUENCE: 38
nnnaccacag ggnnt                                                      15

<210> SEQ ID NO 39
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
     bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
     bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'- bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 39
nnnattaggt cannc                                                     15

<210> SEQ ID NO 40
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 40
nnnggaggcc aannt                                                     15

<210> SEQ ID NO 41
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature

```
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 41
nnnacagaac tgnnc                                                     15

<210> SEQ ID NO 42
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)

<400> SEQUENCE: 42
nnngcagtag aanng                                                     15

<210> SEQ ID NO 43
<211> LENGTH: 15
```

```
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 43
nnngagaagg atnnt                                                      15

<210> SEQ ID NO 44
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
```

```
<222> LOCATION: (14)..(14)
<223> OTHER INFORMATION: n is Adenine having a structure of AmNA (2',4'-
      bridged nucleotide in which R is a methyl group)

<400> SEQUENCE: 44
nnnttgtata aanna                                                        15

<210> SEQ ID NO 45
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 45
nnnttacagt atttnnc                                                      17

<210> SEQ ID NO 46
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
```

```
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 46
nnnttacagt atttggnnt                                                  19

<210> SEQ ID NO 47
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)

<400> SEQUENCE: 47
nnnacagtat ttnnc                                                      15

<210> SEQ ID NO 48
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
```

```
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 48
nnnacagtat ttggnnt                                                    17

<210> SEQ ID NO 49
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 49
nnnacagtat ttggcannt                                                  19

<210> SEQ ID NO 50
<211> LENGTH: 15
<212> TYPE: DNA
```

```
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 50
nnnagtattt ggnnt                                                   15

<210> SEQ ID NO 51
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
```

```
<222> LOCATION: (15)..(16)
<223> OTHER INFORMATION: n is a, c, g, or t

<400> SEQUENCE: 51
nnnagtattt ggcannt                                                 17

<210> SEQ ID NO 52
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 52
nnnagtattt ggcatcnnc                                               19

<210> SEQ ID NO 53
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
```

<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 53
nnnggttaca gtnnt                                                      15

<210> SEQ ID NO 54
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 54
nnnggttaca gtatnng                                                    17

<210> SEQ ID NO 55
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t

```
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 55
nnnggttaca gtatttnnc                                              19

<210> SEQ ID NO 56
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 56
nnnaaggtta canna                                                  15

<210> SEQ ID NO 57
<211> LENGTH: 17
<212> TYPE: DNA
<213> ORGANISM: Artificial Sequence
```

```
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 57
nnnaaggtta cagtnnt                                                17

<210> SEQ ID NO 58
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (17)..(18)
```

<223> OTHER INFORMATION: n is a, c, g, or t

<400> SEQUENCE: 58
nnnaaggtta cagtatnng                                            19

<210> SEQ ID NO 59
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 59
nnntacctca ggtannt                                              17

<210> SEQ ID NO 60
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 60
nnntacctca ggtaatnna                                                19

<210> SEQ ID NO 61
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)

<400> SEQUENCE: 61
nnncatacct cannt                                                    15

<210> SEQ ID NO 62
<211> LENGTH: 17
<212> TYPE: DNA
<213> ORGANISM: Artificial Sequence
<220> FEATURE:
<223> OTHER INFORMATION: Artificial Sequence
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:

```
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 62 nnncataacct caggnna                                                 17

<210> SEQ ID NO 63
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 63 nnncataacct caggtannt                                               19

<210> SEQ ID NO 64
<211> LENGTH: 15
<212> TYPE: DNA
<213> ORGANISM: Artificial Sequence
<220> FEATURE:
```

<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 64
nnntgcatac ctnng                                                  15

<210> SEQ ID NO 65
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 65
nnntgcatac ctcannt                                                    17

<210> SEQ ID NO 66
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 66
nnntgcatac ctcaggnna                                                  19

<210> SEQ ID NO 67
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)

```
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 67
nnncctcagg tannt                                                          15

<210> SEQ ID NO 68
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 68
nnncctcagg taatnna                                                        17

<210> SEQ ID NO 69
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
```

```
<222> LOCATION: (2)..(2)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 69
nnncctcagg taattcnna                                                  19

<210> SEQ ID NO 70
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)

<400> SEQUENCE: 70
nnntcaggta atnna                                                      15

<210> SEQ ID NO 71
<211> LENGTH: 17
<212> TYPE: DNA
<213> ORGANISM: Artificial Sequence
<220> FEATURE:
<223> OTHER INFORMATION: Amido-bridged nucleic acid (AmNA)
```

```
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 71
nnntcaggta attcnna                                                      17

<210> SEQ ID NO 72
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t
```

```
<400> SEQUENCE: 72
nnntcaggta attcacnng                                                19

<210> SEQ ID NO 73
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 73
nnnacaaatg aaatnnc                                                  17

<210> SEQ ID NO 74
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
```

```
      AmNA (2',4'-bridged nucleotide in which R is a methyl group)
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 74
nnnacaaatg aaatttnna                                                19

<210> SEQ ID NO 75
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)

<400> SEQUENCE: 75
nnnaaatgaa atnnc                                                    15

<210> SEQ ID NO 76
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
```

<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 76
nnnaaatgaa atttnna                                                    17

<210> SEQ ID NO 77
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 77
nnnaaatgaa atttcanna                                                  19

<210> SEQ ID NO 78
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:

```
<221> NAME/KEY: modified_base
<222> LOCATION: (1)..(1)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 78
nnnatgaaat ttnna                                                    15

<210> SEQ ID NO 79
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 79
```
nnnatgaaat ttcanna					17

<210> SEQ ID NO 80
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is 5-methylcytosine having a structure of
      AmNA (2',4'-bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 80
nnnatgaaat ttcaacnng					19

<210> SEQ ID NO 81
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)

```
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 81
nnnggacaaa tgnna                                                            15

<210> SEQ ID NO 82
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 82
nnnggacaaa tgaannt                                                          17

<210> SEQ ID NO 83
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
```

AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
       bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
       bridged nucleotide in which R is a methyl group)
<220> FEATURE:
<221> NAME/KEY: modified_base
<222> LOCATION: (14)..(14)
<223> OTHER INFORMATION: n is Thymine having a structure of AmNA (2',4'-
       bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 83
nnnggacaaa tgaaatnnc                                                    19

<210> SEQ ID NO 84
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
       bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
       bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
       bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
       bridged nucleotide in which R is a methyl group)
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Guanine having a structure of AmNA (2',4'-
       bridged nucleotide in which R is a methyl group)

<400> SEQUENCE: 84
nnncaggaca aanna                                                        15

<210> SEQ ID NO 85
<211> LENGTH: 17
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base

```
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)
<220> FEATURE:
<221> NAME/KEY: misc_feature
<222> LOCATION: (15)..(16)
<223> OTHER INFORMATION: n is a, c, g, or t

<400> SEQUENCE: 85
nnncaggaca aatgnna                                                    17

<210> SEQ ID NO 86
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (3)..(3)
<223> OTHER INFORMATION: n is Guanine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Adenine having a structure of AmNA (2',4'-
      bridged nucleotide in which R is a methyl group
<220> FEATURE:
<221> NAME/KEY: modified_base
<222> LOCATION: (14)..(14)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t

<400> SEQUENCE: 86
```

-continued nnncaggaca aatgaannt                                                    19

<210> SEQ ID NO 87
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 87
aggggctgtg aagctgagta                                                   20

<210> SEQ ID NO 88
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 88
ttccaggctg aaaagcagtt                                                   20

<210> SEQ ID NO 89
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 89
gaaacggctt tcagttgagc                                                   20

<210> SEQ ID NO 90
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 90
ctggccatat ccaccagagt                                                   20

<210> SEQ ID NO 91
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 91
tggaattctg gaccaaggag                                                   20

<210> SEQ ID NO 92
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 92
aaagttgggg gagttctcgt                                                   20

<210> SEQ ID NO 93
<211> LENGTH: 20
<212> TYPE: DNA
<213> ORGANISM: Artificial Sequence

```
<220> FEATURE:
<223> OTHER INFORMATION: Amido-bridged nucleic acid (AmNA)

<400> SEQUENCE: 93
gctgaacttg gtgctcttcc                                              20

<210> SEQ ID NO 94
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 94
tagtttggcc accttggttc                                              20

<210> SEQ ID NO 95
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 95
agctgtgtgc ctcttgtgtg                                              20

<210> SEQ ID NO 96
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 96
agttggggat ctctgcattg                                              20

<210> SEQ ID NO 97
<211> LENGTH: 20
<212> TYPE: DNA
<213> ORGANISM: Artificial Sequence
<220> FEATURE:
<223> OTHER INFORMATION: Amido-bridged nucleic acid (AmNA)

<400> SEQUENCE: 97
tcctgcacca ccaactgctt                                              20

<210> SEQ ID NO 98
<211> LENGTH: 19
<212> TYPE: DNA
<213> ORGANISM: Artificial Sequence
<220> FEATURE:
<223> OTHER INFORMATION: Amido-bridged nucleic acid (AmNA)

<400> SEQUENCE: 98
tggcagtgat ggcatggac                                               19

<210> SEQ ID NO 99
<211> LENGTH: 19
<212> TYPE: DNA
<213> ORGANISM: Artificial Sequence
<220> FEATURE:
<223> OTHER INFORMATION: Amido-bridged nucleic acid (AmNA)

<400> SEQUENCE: 99
cagtcgcgtt tgcgactgg                                               19
```

```
<210> SEQ ID NO 100
<211> LENGTH: 19
<212> TYPE: DNA
<213> ORGANISM: Artificial Sequence
<220> FEATURE:
<223> OTHER INFORMATION: Amido-bridged nucleic acid (AmNA)

<400> SEQUENCE: 100
cccactaatg tccagcgtt                                                      19

<210> SEQ ID NO 101
<211> LENGTH: 19
<212> TYPE: DNA
<213> ORGANISM: Artificial Sequence
<220> FEATURE:
<223> OTHER INFORMATION: Amido-bridged nucleic acid (AmNA)

<400> SEQUENCE: 101
gcataacctt tcccatcat                                                      19

<210> SEQ ID NO 102
<211> LENGTH: 19
<212> TYPE: DNA
<213> ORGANISM: Artificial Sequence
<220> FEATURE:
<223> OTHER INFORMATION: Amido-bridged nucleic acid (AmNA)

<400> SEQUENCE: 102
gcgaatactc tgccattat                                                      19

<210> SEQ ID NO 103
<211> LENGTH: 19
<212> TYPE: DNA
<213> ORGANISM: Artificial Sequence
<220> FEATURE:
<223> OTHER INFORMATION: Amido-bridged nucleic acid (AmNA)

<400> SEQUENCE: 103
gccaactaac tctgcagat                                                      19

<210> SEQ ID NO 104
<211> LENGTH: 15
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (13)..(13)
<223> OTHER INFORMATION: n is Thymine having a structure of AmNA (2',4'-
      bridged nucleotide in which R is a methyl group)
```

```
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: n is Adenine having a structure of AmNA (2',4'-
      bridged nucleotide in which R is a methyl group)

<400> SEQUENCE: 104
nnntacctca ggnna                                                          15

<210> SEQ ID NO 105
<211> LENGTH: 19
<212> TYPE: DNA
<213> ORGANISM: Artificial Sequence
<220> FEATURE:
<223> OTHER INFORMATION: Amido-bridged nucleic acid (AmNA)
<220> FEATURE:
<221> NAME/KEY: modified_base
<222> LOCATION: (1)..(1)
<223> OTHER INFORMATION: n is Guanine having a structure of AmNA (2',4'-
      bridged nucleotide in which R is a methyl group)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (2)..(2)
<223> OTHER INFORMATION: n is 5-methylcytosine having a structure of
      AmNA (2',4'-bridged nucleotide in which R is a methyl group)
<220> FEATURE:
<221> NAME/KEY: modified_base
<222> LOCATION: (3)..(3)
<223> OTHER INFORMATION: n is Adenine having a structure of AmNA (2',4'-
      bridged nucleotide in which R is a methyl group)
<220> FEATURE:
<221> NAME/KEY: modified_base
<222> LOCATION: (17)..(17)
<223> OTHER INFORMATION: n is Thymine having a structure of AmNA (2',4'-
      bridged nucleotide in which R is a methyl group)
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: modified_base
<222> LOCATION: (18)..(18)
<223> OTHER INFORMATION: n is 5-methylcytosine having a structure of
      AmNA (2',4'-bridged nucleotide in which R is a methyl group)

<400> SEQUENCE: 105
nnntacctca ggtaatnna                                                      19
```

ANTISENSE OLIGONUCLEOTIDE TARGETING ARL4C MOLECULE, AND NUCLEIC ACID DRUG USING ANTISENSE OLIGONUCLEOTIDE

TECHNICAL FIELD

The present invention relates to an antisense oligonucleotide targeting ARL4C. The present invention also relates to a nucleic acid drug having an antitumor effect using the antisense oligonucleotide.

REFERENCE TO SEQUENCE LISTING

The present application is being filed along with a Sequence Listing in electronic format. The Sequence Listing is provided as a file entitled 59504387_1.TXT, created and last modified on May 6, 2024, which is 109,335 bytes in size. The information in the electronic format of the Sequence Listing is incorporated herein by reference in its entirety.

BACKGROUND ART

ADP-ribosylation factor-like proteins (Arls) constitute one of the subgroups of the small GTP-binding protein superfamily (Non-Patent Document 1). Arf subfamily proteins have been elucidated to play important roles in actin remodeling and regulation of membrane transport pathways (Non-Patent Document 2). However, the functions of most of Arls have not yet been elucidated (Non-Patent Document 3). ARL4C, one of the Arls, is expressed by Wnt/β-catenin signaling and EGF/Ras/mitogen-activated protein kinase (MAPK) signaling, and plays important roles in both of epithelial morphogenesis and tumorigenesis (Non-Patent Documents 4 and 5).

It has been clarified that ARL4C is frequently overexpressed in a colorectal cancer, a lung cancer, and a tongue cancer, but is hardly expressed in a non-tumor area of these tissues (Non-Patent Documents 5 and 6). Further, it is known that in colorectal cancer cells HCT116 and lung adenocarcinoma cells A549, ARL4C expression is increased by Wnt/β-catenin signaling or Ras/MAPK signaling, and hypomethylation of the ARL4C gene increases the ARL4C expression level in lung squamous cell carcinoma cells NCI-H520 (Non-Patent Documents 5 and 6). It is known that in the above-described cancer cells, ARL4C is involved in Rac activation, Rho inhibition, and nuclear localization of YAP and TAZ, and when the expression of ARL4C is suppressed in cancer cells, cell migration, cell infiltration, and cell proliferation are reduced both in vitro and in vivo. Furthermore, it has been also reported that direct injection of siRNA against ARL4C into a xenograft tumor of HCT116 cells transplanted into immunodeficient mice inhibits tumor growth (Non-Patent Document 5). Therefore, it has been suggested that ARL4C may be a novel target molecule in cancer treatment.

On the other hand, conventionally, attempts have been made to use oligonucleotides such as antisense oligonucleotides, siRNAs, aptamers, and miRNAs for the treatment of intractable diseases. Currently, antisense oligonucleotide-based therapeutic agents are approved in the United States for cytomegalovirus retinitis, age-related macular degeneration, familial hypercholesterolemia homozygotes, Duchenne muscular dystrophy, and spinal muscular atrophy (Non-Patent Document 7).

In addition, therapeutic agents using oligonucleotides are sensitive to nuclease degradation, and after being systemically administered, the therapeutic agents may be inefficiently delivered to target cells in some cases, which poses a barrier to practical use of the same. Therefore, conventionally, it has been energetically studied to overcome such a barrier by chemically modifying an oligonucleotide. For example, it is known that when 2',4'-bridged nucleic acids (LNA) and phosphorothioate bonds are introduced into an antisense oligonucleotide, the antisense oligonucleotide thus obtained has a high binding ability to the target RNA, thereby having excellent nuclease resistance and pharmacokinetics. It also has been reported that among 2',4'-bridged nucleic acids, bridged nucleic acids in which a cyclic amide structure is inserted (AmNA) can further improve the binding ability to a target RNA, the nuclease resistance, and the pharmacokinetics. (Non-patent document 8)

However, in the prior art, if the antisense oligonucleotide is chemically modified according to a molecular design thereof based on the base sequence of the target gene, it is unlikely that a sufficient effect would be achieved in vitro; even if a sufficient effect is achieved in vitro, a sufficient effect cannot be achieved in vivo. As mentioned above, it has been suggested that ARL4C can be a novel target molecule in cancer treatment, and methods for chemical modification of oligonucleotides have been developed; however, as to antisense oligonucleotides targeting ARL4C, a clinically practical product used in cancer treatment has not been developed.

PRIOR ART DOCUMENTS

Non-Patent Document

Non-Patent Document 1: Matsumoto S. et al., Arl4c is a key regulator of tubulogenesis and tumourigenesis as a target gene of Wnt-β-catenin and growth factor-Ras signalling. J Biochem 2017; 161: 27-35.
Non-Patent Document 2: D'Souza-Schorey C et al., ARF proteins: roles in membrane traffic and beyond. Nat Rev Mol Cell Biol 2006; 7: 347-58.
Non-Patent Document 3: Burd C G. et al., Arf-like GTPases: not so Arf-like after all. Trends Cell Biol 2004; 14: 687-94.
Non-Patent Document 4: Matsumoto S. et al., A combination of Wnt and growth factor signaling induces Arl4c expression to form epithelial tubular structures. EMBO J 2014; 33: 702-18.
Non-Patent Document 5: Fujii S. et al., Arl4c expression in colorectal and lung cancers promotes tumorigenesis and may represent a novel therapeutic target. Oncogene 2015; 34: 4834-44.
Non-Patent Document 6: Fujii S. et al., Epigenetic upregulation of ARL4C, due to DNA hypomethylation in the 3'-untranslated region, promotes tumorigenesis of lung squamous cell carcinoma. Oncotarget 2016; 7: 81571-87.
Non-Patent Document 7: Stein C A. et al., FDA-Approved Oligonucleotide Therapies in 2017. Mol Ther 2017; 25: 1069-75.
Non-Patent Document 8: Yahara A. et al., Amido-bridged nucleic acids (AmNAs): synthesis, duplex stability, nuclease resistance, and in vitro antisense potency. Chembiochem 2012; 13: 2513-6.

SUMMARY OF THE INVENTION

Problems to be Solved by the Invention

It is an object of the present invention to provide an antisense oligonucleotide that targets ARL4C and exerts an antitumor effect in vivo, as well as to provide a nucleic acid drug using the antisense oligonucleotide.

Means for Solving the Problem

As a result of diligent studies to solve the above problems, the present inventors have found that an antisense oligonucleotide including a sequence of 10 or more consecutive bases that are included in the base sequence represented by SEQ ID NO: 1 suppresses the expression of ARL4C in tumor cells in vitro, thereby suppressing the migration and proliferation of the same, and that systemic administration of the above-described antisense oligonucleotides exerts an excellent antitumor effect even in vivo. The present invention has been completed by further studies based on such findings.

That is, the present invention provides the inventions of the following aspects.

Item 1. An antisense oligonucleotide targeting ARL4C, including a sequence of 10 or more consecutive bases that are included in the base sequence represented by SEQ ID NO: 1.

Item 2. The antisense oligonucleotide according to Item 1, wherein the number of bases constituting the antisense oligonucleotide is 10 to 50.

Item 3. The antisense oligonucleotide according to Item 1 or 2,
wherein the sequence includes the base sequence represented by SEQ ID NO: 1.

Item 4. The antisense oligonucleotide according to any one of Items 1 to 3, consisting of the base sequence represented by SEQ ID NO: 1 or 2.

Item 5. The antisense oligonucleotide according to any one of Items 1 to 4,
wherein at least one nucleotide is a 2',4'-bridged nucleotide.

Item 6. The antisense oligonucleotide according to any one of Items 1 to 5,
wherein the 2',4'-bridged nucleotide has a structure shown in General Formula (1) shown below:

[Chemical Formula 1]

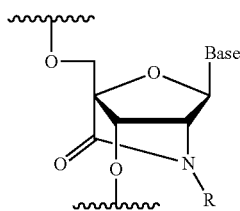

(1)

where "Base" represents a purine-9-yl group or a 2-oxo-1,2-dihydropyrimidine-1-yl group which may be substituted with a substituent, and "R" represents: a hydrogen atom; an alkyl group having 1 to 7 carbon atoms wherein the alkyl group may be branched or may form a ring; an alkenyl group having 2 to 7 carbon atoms wherein the alkenyl group may be branched or may form a ring; an aryl group having 3 to 12 carbon atoms wherein the aryl group may have a substituent and may include a heteroatom; and an aralkyl group having an aryl moiety having 3 to 12 carbon atoms wherein the aryl moiety may have a substituent and may include a heteroatom.

Item 7. The antisense oligonucleotide according to any one of Items 1 to 6, wherein at least one of internucleoside bonds is a phosphorothioate bond.

Item 8. The antisense oligonucleotide according to any one of Items 1 to 7,
wherein all of internucleoside bonds are phosphorothioate bonds, and
the 1st to 3rd nucleotides from the 5'-terminal and the 2nd and 3rd nucleotides from the 3'-terminal are 2',4'-bridged nucleotides.

Item 9. The antisense oligonucleotide according to any one of Items 1 to 8, the antisense oligonucleotide being a chemically modified antisense oligonucleotide consisting of Sequence A or Sequence B shown below:
Sequence A: G(Y)^5(Y)^A(Y)^t^a^c^c^t^c^a^g^g^T(Y)^A(Y)^a SEQ ID NO: 104);
Sequence B: G(Y)^5(Y)^A(Y)^t^a^c^c^t^c^a^g^g^t^a^a^t^T(Y)^5(Y)^a (SEQ ID NO: 105)
where "G(Y)" represents guanine having a structure of AmNA (2',4'-bridged nucleotide in which R is a methyl group in General Formula (1) described above),
"A(Y)" represents adenine having a structure of AmNA,
"T(Y)" represents thymine having a structure of AmNA,
"5(Y)" represents 5-methylcytosine having a structure of AmNA, and
"^" represents a phosphorothioate bond.

Item 10. A nucleic acid drug containing the antisense oligonucleotide according to any one of Items 1 to 9.

Item 11. The nucleic acid drug according to Item 10, for use as an antitumor agent.

Item 12. The nucleic acid drug according to Item 10 or 11, for use in treatment of a liver cancer, a large intestine cancer, a lung cancer, or a tongue cancer.

Item 13. The nucleic acid drug according to Item 10, for use in treatment of a metastatic liver cancer, or treatment of a cancer metastatic from a pancreatic cancer.

Item 14. Use of the antisense oligonucleotide according to any one of Items 1 to 9 for the manufacture of an antitumor agent.

Item 15. A method for treating a tumor, including:
administering, to a tumor patient, a therapeutically effective amount of the antisense oligonucleotide according to any one of Items 1 to 9.

Advantages of the Invention

The antisense oligonucleotide of the present invention targets ARL4C and effectively suppresses the expression or function of ARL4C, thereby being capable of suppressing the proliferation of tumor cells effectively. The antisense oligonucleotide of the present invention not only has therapeutic effects on primary tumors, but also is capable of preventing or treating metastatic tumors.

In addition, the antisense oligonucleotide of the present invention exhibits a particularly excellent antitumor effect on tumors in which ARL4C is highly expressed, and since it is a nucleic acid drug, it has a property of easily accumulating in the liver by systemic administration. On the other hand, since ARL4C is frequently highly expressed in a liver cancer and a lung cancer, the antisense oligonucleotide of the present invention is particularly effective for the treatment of a liver cancer or a lung cancer, and the prevention or treatment of a metastatic liver cancer. Furthermore, the antisense oligonucleotide of the present invention is also effective in preventing or treating a cancer metastatic from a pancreatic cancer.

In addition, since ARL4C is highly expressed in a tumor cell-specific manner, the antisense oligonucleotide of the present invention has high tumor specificity and is also excellent in terms of safety.

EMBODIMENTS OF THE INVENTION

1. Definition

Figure 1:
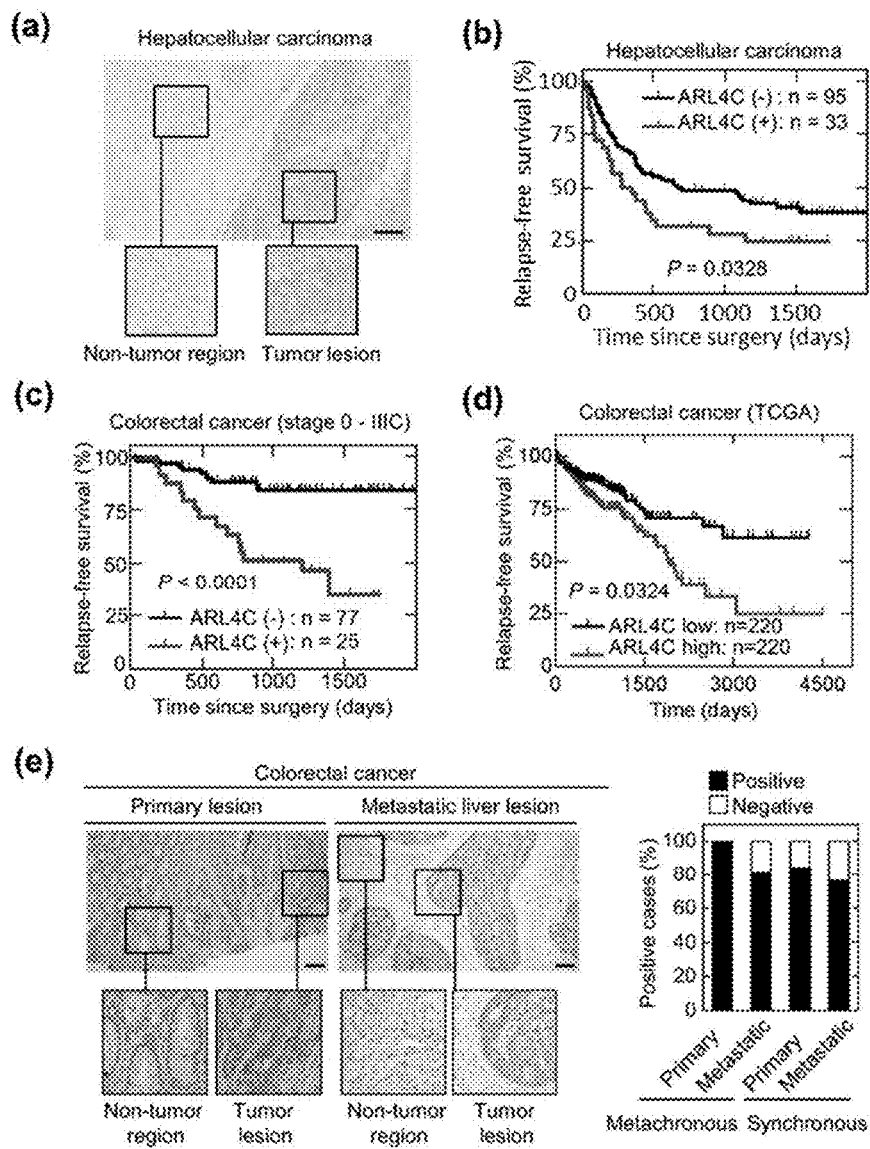
FIG. 1 (a) shows an image of an ARL4C-positive primary liver cancer immunostained with anti-ARL4C antibody. (b) shows the results obtained by analyzing the relationship between the recurrence-free survival rate and the ARL4C expression in liver cancer patients. (c) shows the results obtained by analyzing the relationship between the recurrence-free survival rate and the ARL4C expression in colorectal cancer patients. (d) shows the results obtained by analyzing the relationship between ARL4C expression and overall survival rate, using the TCGA data set. (e) shows the results obtained by immunohistological measuring ARL4C expression in tumors resulting from metastasis of colorectal cancers to the livers.

In the present specification, antisense oligonucleotides may be abbreviated as "ASO".

The base sequence of the nucleic acid (ASO, etc.) shown in the present specification has a 5'-terminal at the left end and a 3'-terminal at the right end.

2. Antisense Oligonucleotide

The ASO of the present invention is an ASO that targets ARL4C and is characterized by including a sequence of 10 or more consecutive bases that are included in "gcatacctcaggtaa" (SEQ ID NO: 1). Hereinafter, the ASO of the present invention will be described in detail.

[Target Molecule]

The ASO of the present invention is an ASO that targets ARL4C (ARL4C ASO), and is a nucleic acid molecule capable of exerting an antitumor effect by suppressing the expression of ARL4C.

The mRNA of human ARL4C has the base sequence represented by SEQ ID NO: 3, and the base sequence represented by SEQ ID NO: 1 is complementary to the base sequence from the 1316th site to the 1330th site in SEQ ID NO: 3.

[Base Sequence]

The ASO of the present invention includes, as a base sequence, a sequence of 10 or more consecutive bases that are included in "gcatacctcaggtaa" (SEQ ID NO: 1). By including such a specific base sequence, the ASO can effectively suppress the expression of ARL4C and effectively exert an antitumor effect in vivo.

The number of bases of the ASO of the present invention is not particularly limited as long as the ASO includes a sequence of 10 or more consecutive bases that are included in the base sequence represented by SEQ ID NO: 1 and can knock down ARL4C; however, the number of bases of the ASO is preferably 13 or more. More specifically, the number of bases of the ASO is, for example, 10 to 50, preferably 10 to 40, more preferably 12 to 30, still more preferably 15 to 20, still more preferably 15 to 19, particularly preferably 15 to 17, and most preferably 15 (that is, the ASO consists of the base sequence represented by SEQ ID NO: 1).

When the number of bases of the ASO of the present invention is 10 to 14, the base sequence of the ASO of the present invention may be set to a base sequences having 10 to 14 consecutive bases included in the base sequence represented by SEQ ID NO: 1.

When the number of bases of the ASO of the present invention is 15, the base sequence of the ASO of the present invention may be set to one consisting of the base sequence represented by SEQ ID NO: 1.

When the number of bases of the ASO of the present invention is 16 or more, the base sequence of the ASO of the present invention includes the base sequence represented by SEQ ID NO: 1, with one or more bases being linked thereto on the 5'-terminal side and/or the 3'-terminal side. The type of the one or more bases linked to the 5'-terminal side and/or the 3'-terminal side is not particularly limited as long as ARL4C can be knocked down; the type can be set appropriately based on the base sequence of the mRNA of ARL4C as the target molecule.

From the viewpoint of further improving the antitumor effect exerted in the living body, the ASO of the present invention is, for example, an ASO consisting of the base sequence represented by SEQ ID NO: 1 or 2, and more preferably, an ASO consisting of the base sequence represented by SEQ ID NO: 1.

[Chemical Modification]

The ASO of the present invention may be a chemically unmodified ASO (that is, an ASO consisting of natural nucleotides); however, it is desirable that the ASO is chemically modified so that the resistance to a nuclease, the affinity to a target gene, the pharmacokinetics, etc. are increased or improved.

In chemically modifying the ASO of the present invention, at least one part of the nucleotide among the base moiety, the sugar moiety, and the internucleoside bond may be chemically modified, and it is desirable that all of the nucleotides are chemically modified.

The nucleotide in which the base moiety is chemically modified is, for example, a nucleotide in which a substituent is introduced into the base moiety. Specific examples of the substituent include a hydroxyl group, a linear alkyl group having 1 to 6 carbon atoms, a linear alkoxy group having 1 to 6 carbon atoms, a mercapto group, a linear alkylthio group having 1 to 6 carbon atoms, an amino group, a linear alkylamino group having 1 to 6 carbon atoms, and a halogen atom. When the base is cytosine (C), preferable examples of chemically modified cytosine include 5-methylcytidine and 2'-O-methylcytidine.

Examples of the nucleotide in which the sugar moiety is chemically modified include: a 2',4'-bridged nucleotides (bridged nucleic acid, BNA); and a nucleotide in which the hydroxyl group at the 2' position of the sugar moiety is substituted with an alkoxy group (for example, an alkoxy group having 1 to 5 carbon atoms such as a methoxy group or an ethoxy group), or with a halogen atom (a fluorine atom, etc.). Among these, a 2',4'-bridged nucleotide is preferred, for example.

A preferable example of the 2',4'-bridged nucleotide is a nucleotide having the structure shown in General Formula (1) below.

[Chemical Formula 2]

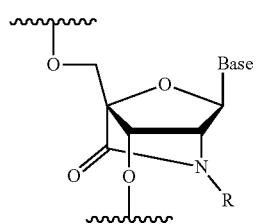

(1)

In General Formula (1), "Base" represents a base corresponding to the base sequence, and specifically, a purine-9-yl group or a 2-oxo-1,2-dihydropyrimidine-1-yl group that may be substituted with a substituent. Specific examples of the substituent include a hydroxyl group, a linear alkyl group having 1 to 6 carbon atoms, a linear alkoxy group having 1 to 6 carbon atoms, a mercapto group, a linear alkylthio group having 1 to 6 carbon atoms, an amino group, a linear alkylamino group having 1 to 6 carbon atoms, and a halogen atom.

Further, specific examples of the "Base" in General Formula (1) include: 6-aminopurine-9-yl group that may be substituted with a substituent, in a case where the base is adenine (A); 2-amino-6-hydroxypurine-9-yl group that may be substituted with a substituent, in a case where the base is guanine (G); 2-oxo-4-amino-1,2-dihydropyrimidine-1-yl group (e.g., 4-amino-5-methyl-2-oxo-1,2-dihydropyrimidine-1-yl group (including 5-methylcytosine-1-yl group, 2'-O-methylcytosine-1-yl group, and the like) that may be substituted with a substituent, in a case where the base is cytosine (C); 2-oxo-4-hydroxy-5-methyl-1,2-dihydropyrimidine-1-yl group that may be substituted with a substituent, in a case where the base is thymine (T).

In General Formula (1), "R" represents a hydrogen atom; an alkyl group having 1 to 7 carbon atoms wherein the alkyl group may be branched or may form a ring; an alkenyl group having 2 to 7 carbon atoms wherein the alkenyl group may be branched or may form a ring; an aryl group having 3 to 12 carbon atoms wherein the aryl group may have a substituent and may include a heteroatom; and an aralkyl group having an aryl moiety having 3 to 12 carbon atoms wherein the aryl moiety may have a substituent and may include a heteroatom. Specific examples of the substituent that can be included in the aryl group or the aralkyl group include a hydroxyl group, a linear alkyl group having 1 to 6 carbon atoms, a linear alkoxy group having 1 to 6 carbon atoms, a mercapto group, a linear alkylthio group having 1 to 6 carbon atoms, an amino group, a linear alkylamino group having 1 to 6 carbon atoms, and a halogen atom. "R" is preferably a hydrogen atom, a methyl group, an ethyl group, an n-propyl group, an isopropyl group, a phenyl group, or a benzyl group; it is more preferably a hydrogen atom or a methyl group, and particularly preferably a methyl group. In the present specification, the 2',4'-bridged nucleotide in which R in General Formula (1) is a methyl group is referred to as "AmNA" in some cases.

Further, another example of the 2',4'-bridged nucleotide is a nucleotide having a structure shown in General Formula (2) below. The nucleotide is a known 2',4'-bridged nucleotide, which is also called a guanidine bridged nucleic acid (WO2014/046212).

[Chemical Formula 3]

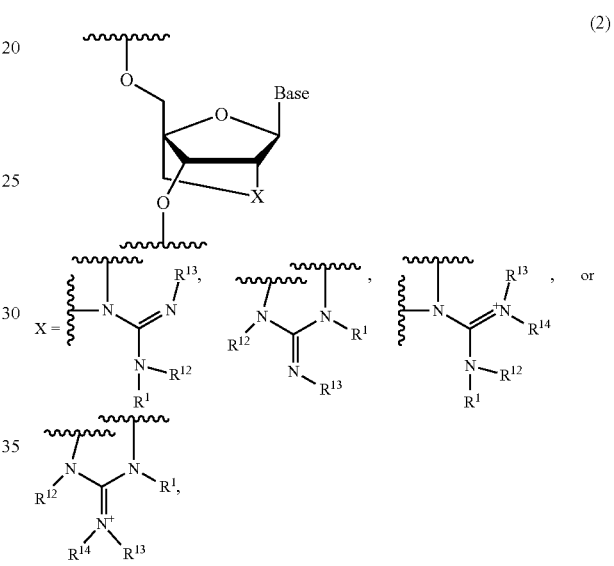

(2)

In General Formula (2), "Base" represents the same one as that represented by "Base" in General Formula (1) described above. In General Formula (2), $R^1$, $R^{12}$, and $R^{13}$ each identically or differently represent a hydrogen atom; an alkyl group having 1 to 7 carbon atoms wherein the alkyl group may be branched or may form a ring, and $R^{14}$ represents a hydrogen atom.

Further, another example of the 2',4'-bridged nucleotide is a nucleotide having a structure shown in General Formula (3) below. The nucleotide is a known 2',4'-bridged nucleotide, which is also called a spirocyclopropane bridged nucleic acid (WO2015/125783).

[Chemical Formula 4]

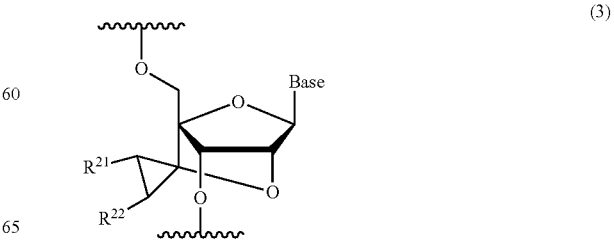

(3)

In General Formula (3), "Base" represents the same one as that represented by "Base" in General Formula (1) described above. Further, in General Formula (3), $R^{21}$ and $R^{22}$ each identically or differently represent a hydrogen atom; an alkyl group having 1 to 7 carbon atoms that may be substituted with an aryl group having 3 to 12 carbon atoms that may include a heteroatom, and that may be branched or may form a ring; or an aralkyl group having an aryl moiety having 3 to 12 carbon atoms wherein the aryl moiety may include a heteroatom. Alternatively, $R^{21}$ and $R^{22}$ together form a group of —$(CH_2)_n$— [where n is an integer of 2 to 5].

Further, another example of the 2',4'-bridged nucleotide is a nucleotide having a structure shown in General Formula (4) or (4') below. The nucleotide is a known 2',4'-bridged nucleotide, which is also called an ethyleneoxy-bridged nucleic acid (WO2016/017422).

[Chemical Formula 5]

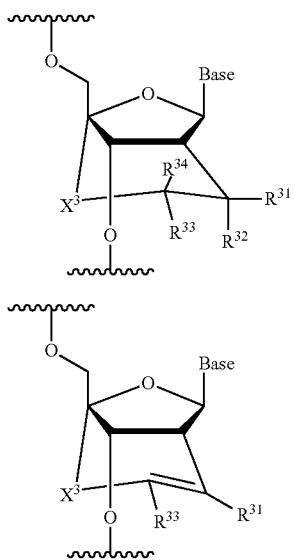

In General Formulae (4) and (4'), "Base" represents the same one as that represented by "Base" in General Formula (1) described above. Further, in General Formulae (4) and (4'), $X^3$ represents an oxygen atom or a sulfur atom.

In General Formulae (4) and (4'), $R^{31}$ and $R^{32}$ each identically or differently represent a hydrogen atom; an alkyl group having 1 to 7 carbon atoms wherein the alkyl group may be branched or may form a ring; an alkoxy group having 1 to 7 carbon atoms wherein the alkoxy group may be branched or may form a ring; or an amino group.

Further, in the case of General Formula (4), $R^{31}$ and $R^{32}$ together may form —$C(R^{35})R^{36}$ [where $R^{35}$ and $R^{36}$ each identically or differently represent a hydrogen atom; a hydroxyl group; a mercapto group; an amino group; a linear or branched alkoxy group having 1 to 6 carbon atoms; a linear or branched alkylthio group having 1 to 6 carbon atoms; a cyanoalkoxy group having 1 to 6 carbon atoms; or a linear or branched alkylamino group having 1 to 6 carbon atoms].

In General Formulae (4) and (4'), $R^{33}$ represents a hydrogen atom; an alkyl group having 1 to 7 carbon atoms wherein the alkyl group may be branched or may form a ring; an alkoxy group having 1 to 7 carbon atoms wherein the alkoxy group may be branched or may form a ring; or a linear or branched alkylthio group having 1 to 6 carbon atoms.

In General Formula (4), $R^{34}$ represents a hydrogen atom; an alkyl group having 1 to 7 carbon atoms wherein the alkyl group may be branched or may form a ring; an alkoxy group having 1 to 7 carbon atoms wherein the alkoxy group may be branched or may form a ring; or a linear or branched alkylthio group having 1 to 6 carbon atoms.

Furthermore, other examples of 2',4'-bridged nucleotides include those having the structures shown below. "Base" and "R" in the following structural formulae represent the same ones as those represented by "Base" and "R" in General Formula (1) described above, respectively.

[Chemical Formula 6]

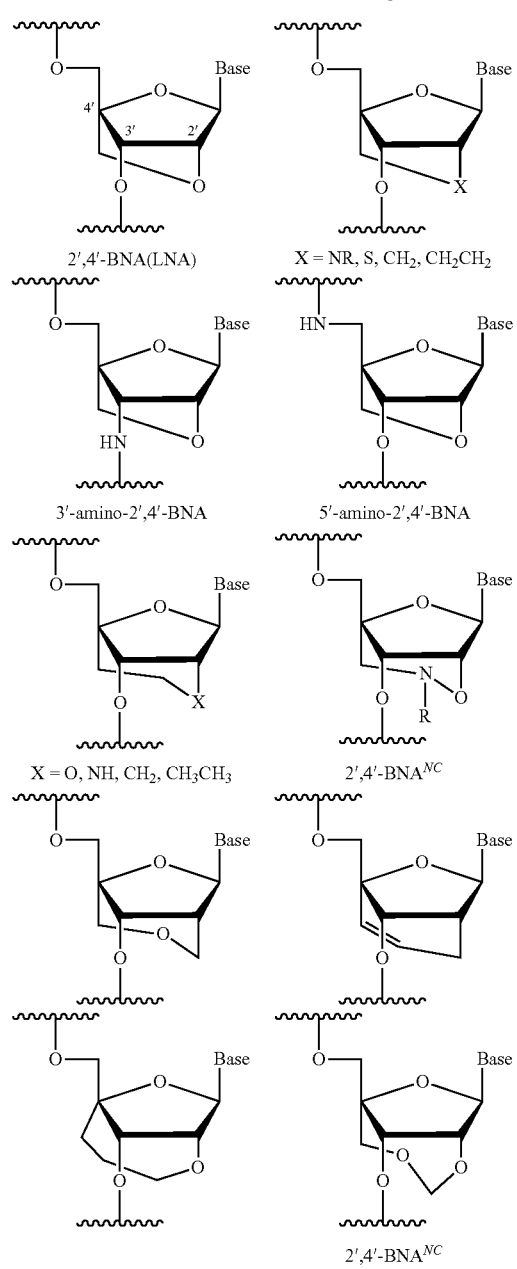

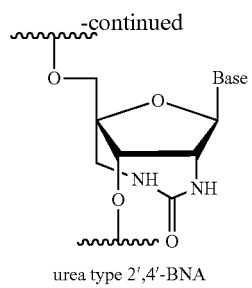

urea type 2',4'-BNA

As for the chemical modification of the internucleoside bond, the internucleoside bond is a bond of, for example, phosphorothioate, chiral phosphorothioate, phosphorodithioate, phosphotriester, aminoalkylphosphotriester, 3'-alkylene phosphonate, 5'-alkylene phosphonate, phosphinate, 3'-aminophosphoramidate, aminoalkylphosphoramidate, thionophosphoramidate, thionoalkylphosphonate, thionoalkylphosphotriester, selenophosphate, or boranophosphate. The chemical modification of the internucleoside bond is preferably phosphorothioate, for example.

In the ASO of the present invention, the chemical modification may be applied to some of the nucleosides and/or the internucleoside bonds, or may be applied to all of the nucleosides and/or the internucleoside bonds.

Preferable examples of the chemical modification applied to the ASO of the present invention include chemical modification obtained by including at least one, preferably one to ten, more preferably two to eight, still more preferably two to six, or particularly preferably five 2',4'-bridged nucleotides. In addition, in a case where a 2',4'-bridged nucleotide is included, for example, it is preferable that the 1st to 3rd nucleotides from the 5'-terminal and the 2nd and 3rd nucleotides from the 3'-terminal are 2',4'-bridged nucleotides (preferably AmNAs).

In addition, in a preferable example of the chemical modification applied to the ASO of the present invention, at least one of the internucleoside bonds is a phosphorothioate bond. Further, in a preferable example in a case where a phosphorothioate bond is included, preferably 50% or more, more preferably 80% or more, still more preferably 90% or more, particularly preferably 100% (i.e., all), among the total, i.e., 100%, of the internucleoside bonds, are phosphorothioate bonds.

A preferable example of the ASO of the present invention is a chemically modified ASO wherein all of the internucleoside bonds are phosphorothioate bonds, and the 1st to 3rd nucleotides from the 5'-terminal side and the 2nd and 3rd nucleotides from the 3'-terminal side are 2',4'-bridged nucleotides (preferably AmNAs).

A preferable specific example of the ASO of the present invention is a chemically modified ASO consisting of the following sequence A or B. The chemically modified ASO consisting of the following sequence A or B can suppress the expression of ARL4C remarkably effectively, thereby having a particularly excellent antitumor effect in vivo; thus, it can be used particularly preferably.

Sequence A: G(Y)^5(Y)^A(Y)^t^a^c^c^t^c^a^g^g^T(Y)^A(Y)^a (SEQ ID NO: 104);
Sequence B: G(Y)^5(Y)^A(Y)^t^a^c^c^t^c^a^g^g^t^a^a^t^T(Y)^5(Y)^a (SEQ ID NO: 105)

In the sequences A and B, "G(Y)" represents guanine having an AmNA structure (2',4'-bridged nucleotide in which R is a methyl group in General Formula (1) described above), "A(Y)" represents adenine having an AmNA structure, "T(Y)" represents thymine having an AmNA structure, "5(Y)" represents 5-methylcytosine having an AmNA structure, and "^" represents a phosphorothioate bond.

[Use/Application Method]

The ASO of the present invention acts on ARL4C as a target molecule, suppresses the expression, migration, and growth of ARL4C in tumor cells, and exerts an excellent antitumor effect. Therefore, it can be used as a nucleic acid drug that is administered as an antitumor agent to tumor patients.

The ASO of the present invention can exert an excellent antitumor effect on both primary tumors and metastatic tumors. The primary tumor or metastatic tumor to which the ASO of the present invention is applicable is not particularly limited; specific examples of the tumor include solid cancers such as liver cancer, metastatic liver cancer, colorectal cancer, lung cancer, tongue cancer, pancreatic cancer, gastric cancer, colon cancer, rectal cancer, bladder cancer, prostate cancer, cervical cancer, head and neck cancer, bile duct cancer, gallbladder cancer, oral cancer, pharyngeal cancer, laryngeal cancer, brain cancer, glioma, anti-blastoma, polymorphic glioblastoma, sarcoma, malignant melanoma, renal cancer, and thyroid cancer; and hematological cancers such as leukemia and malignant lymphoma.

Upon co-activation of the Wnt/β-catenin signal and the EGF/Ras-MAPK signal, ARL4C is highly expressed in a tumor cell-specific manner, and by regulating the activities of Rac and Rho, ARL4C exhibits an effect of promoting the motility and the infiltration ability of tumor cells, and tumorigenesis. On the other hand, the ASO of the present invention effectively suppresses the proliferation of tumor cells by inhibiting the expression of ARL4C in a tumor in which ARL4C is highly expressed; therefore, the cancer expressing ARL4C can be regarded as a target to which the present invention is suitably applied. In particular, a liver cancer, a colorectal cancer, a lung cancer, and a tongue cancer have high expression of ARL4C at high frequency, and therefore, the ASO of the present invention is particularly suitably applied to these cancers. In addition, since the liver is an organ in which systemically administered nucleic acid drugs are likely to accumulate, it can be said that a liver cancer is particularly suitable as a target to which the ASO of the present invention is to be applied.

As for a tumor having high expression of ARL4C, the expression can be confirmed by performing tissue immunization with respect to a tissue collected from the tumor. Specifically, a collected tumor tissue is immunostained with an anti-ARL4C antibody, and when the expression of ARL4C is observed in 20% or more of the tumor area, it is determined that ARL4C is highly expressed.

As described above, since the liver is an organ in which systemically administered nucleic acid drugs are likely to accumulate, a metastatic liver cancer is a suitable example of a metastatic tumor as a target to be prevented or treated by the ASO of the present invention. Further, another suitable example of a metastatic tumor as a target to be prevented or treated by the ASO of the present invention is a cancer metastatic from a pancreatic cancer.

The ASO of the present invention is suitably used as a nucleic acid drug for humans.

The method for administering ASO of the present invention is not particularly limited as long as an antitumor effect can be obtained; examples of the method include systemic administration such as intravenous injection, subcutaneous injection, intramuscular injection, and intraperitoneal injection, as well as local administration such as local injection into the affected area, transpulmonary administration, and suppository administration.

Regarding the dose of ASO of the present invention, the therapeutically effective amount may be appropriately set according to the type of an active ingredient to be used, the administration form, the type of a tumor to which the ASO is to be applied, the degree of symptom of a patient, and the like. For example, the single dose of ASO of the present invention is usually set to about 100 µg to 100 mg/kg body weight, and may be administered at a frequency of about once every 3 to 7 days.

In addition, the ASO of the present invention may be used alone, or may be used in combination with one, two, or more other drugs having antitumor activity and/or radiation therapy.

[Formulation]

The ASO of the present invention is prepared in a formulation according to the administration form, and is used as a nucleic acid drug. Examples of the formulation of the nucleic acid drug containing ASO of the present invention include liquid-type preparations such as liquid agents, suspension preparations, and liposome preparations.

In addition, the nucleic acid drug containing ASO of the present invention is formulated according to the formulation form thereof, with a pharmaceutically acceptable carrier or additive being added thereto. For example, in the case of making a liquid-type preparation, it can be prepared using physiological saline, a buffer solution, or the like.

Further, it is desirable that the nucleic acid drug containing the ASO of the present invention is formulated together with a nucleic acid transfer agent so that the ASO can be easily transferred into tumor cells. Specific examples of the nucleic acid transfer agent include lipofectamine, oligofectamine, RNAiFect, liposome, polyamine, DEAE dextran, calcium phosphate, and dendrimer.

EXAMPLES

Hereinafter, the present invention will be described in more detail with reference to examples. However, the present invention is not construed as being limited to the following examples.

1. Test Material and Test Method 1-1. Patients and Cancer Tissues

This study was conducted on 128 liver cancer patients (Stages I to IVA) aged 21 to 81 (average 69 years old) who underwent surgical resection between January 2010 and December 2012 at Kobe University Hospital, and 115 colorectal cancer patients aged 28 to 91 (average 66 years old) who underwent surgical resection between February 2007 and February 2017 at Osaka University Hospital. Of the colorectal cancer patients, 102 patients were in Stages 0 to IIIC and 13 patients were in Stages IVA to IVB. Tumors were classified according to the Union for International Cancer Control (UICC) TNM classification. Resected specimens were macroscopically examined so that the location and size of the tumor were determined. Histological specimens were fixed with 10% by volume of formalin and embedded in paraffin. From each specimen, a 4 µm thick section was produced, and stained with hematoxylin and eosin (HE), or immunoperoxidase, for each analysis. The protocol in this study was carried out under the approval of the Medical Ethics Committee of Kobe University Graduate School of Medicine, etc. (No. 180048) and the approval of the Osaka University Graduate School of Medicine (No. 13032).

1-2. Immunohistochemical Test

The immunohistochemical test was carried out by improving the method reported by Fujii S et al. (Oncogene 2015; 34: 4834-44). When 20% or more of the total area of the tumor lesion was stained with ARL4C, it was judged to be ARL4C positive.

1-3. Materials

Liver cancer cells (HLE, HLF, HuH-7, and PLC) were purchased from the Cell Resource Center for Biomedical Research, Institute of Development, Aging and Cancer, Tohoku University. HepG2 cells were purchased from the American Type Culture Collection (ATCC). HCT116 cells were supplied by Dr. T. Kobayashi (Hiroshima University). A549 cells were supplied by Dr. Y. Shintani (Osaka University). S2-CP8 cells were supplied by the Cell Resource Center for Biomedical Research, Institute of Development, Aging and Cancer, Tohoku University.

HLE, HLF, HuH-7, PLC, HCT116, A549, and S2-CP8 cells were grown in Dulbecco's modified Eagle's medium (DMEM) containing 10% fetal bovine serum (FBS). HepG2 cells were grown in Eagle's minimal essential medium (E-MEM) containing GlutaMAX™ I (Life Technologies, Darmstadt, Germany, catalog 35050-061), MEM non-essential amino acids (Life Technologies, catalog 11140-050), and 10% FBS.

HLE cells allowing for the stable expression of GFP (HLE/GFP cells), HLE cells allowing for the stable expression of ARL4c-GFP with GFP fused to the C-terminal side (HLE/ARL4C-GFP cells, i.e., cells in which ARL4C-GFP is transduced and stably expressed), HCT116 cells allowing for the stable expression of luciferase (HCT116/Luc cells), A549 cells allowing for the stable expression of luciferase (A549/Luc cells), and S2-CP8 cells allowing for the stable expression of luciferase (S2-CP8/Luc cells) were produced using lentivirus according to the method reported by Matsumoto S et al. (EMBO J 2014; 33: 702-18) and Fujii S et al. (Oncogene 2015; 34: 4834-44). In addition, ARL4C-GFP is ARL4C with GFP fused thereto.

Anti-ARL4C and anti-PIK3CD antibodies were purchased from Abcam (Cambridge, UK) and Santa Cruz Biotechnology (Santa Cruz, CA, USA), respectively. Anti-phosphorylated AKT (S473) antibody, anti-AKT antibody, anti-Ki-67 antibody, and anti-YAP/TAZ were purchased from Cell Signaling Technology (Beverly, MA, USA). PD184161 (MEK1/2 inhibitor) and VivoGlo luciferin were purchased from Sigma-Aldrich (Steinheim, Germany) and Promega (Madison, WI, USA), respectively.

1-4. Preparation of ASO targeting ARL4C 15 mer or 19 mer ASOs in which AmNA monomers were contained and linking was achieved by phosphodiester bonds, and 6-carboxyfluorescein (FAM)-labeled ASOs, were synthesized by Gene Design Co., Ltd. according to the method reported in Yahara A et al. (J Pharmacol Exp Ther 2012; 343: 489-96.) And Zuker M (Nucleic Acids Res 2003; 31: 3406-15).

The sequences of the prepared ASOs targeting ARL4C are shown in Table 1.

In the present specification and drawings, among the ASOs shown in Table 1, "hArl4c-1316-AmNA (15)" is referred to as "ASO-1316"; "hArl4c-1312-AmNA (19)" as "ASO-1312"; "hArl4c-650-AmNA (15)" as "ASO-650"; "hArl4c-793-AmNA (15)" as "ASO-793"; "hArl4c-986-AmNA (15)" as "ASO-986"; "hArl4c-1065-AmNA (15)" as "ASO-1065"; "hArl4c-1454-AmNA (15)" as "ASO-1454"; "hArl4c-3225-AmNA (15)" as "ASO-"; "3225" "hArl4c-1450-AmNA (19)" as "ASO-1450"; and "hArl4c-3223-AmNA (19)" as "ASO-3223" in some cases.

ASO-1316 consists of the base sequence represented by SEQ ID NO: 1, and ASO-1312 consists of the base sequence represented by SEQ ID NO: 2.

TABLE 1

| Sequence Name (Number of Bases) | Sequence (5'→3') | SEQ ID NO |
|---|---|---|
| Control ASO | T(Y)^a^g^A(Y)^g^a^G(Y)^t^a^5(Y)^c^c^A(Y)^t^c | 4 |
| hAr14c-1-AmNA(15) | G(Y)^G(Y)^5(Y)^a^g^c^c^t^c^a^c^a^G(Y)^T(Y)^c | 5 |
| hAr14c-88-AmNA(15) | G(Y)^5(Y)^5(Y)^t^c^t^g^g^c^c^t^g^G(Y)^G(Y)^a | 6 |
| hAr14c-474-AmNA(15) | G(Y)^T(Y)^T(Y)^a^g^a^g^g^a^g^a^t^G(Y)^T(Y)^t | 7 |
| hAr14c-650-AmNA(15) (ASO-650) | A(Y)^A(Y)^G(Y)^t^g^g^c^a^g^c^t^g^A(Y)^T(Y)^g | 8 |
| hAr14c-793-AmNA(15) (ASO-793) | A(Y)^5(Y)^T(Y)^t^g^g^t^c^a^c^c^t^T(Y)^G(Y)^t | 9 |
| hAr14c-986-AmNA(15) (ASO-986) | A(Y)^T(Y)^5(Y)^t^c^a^t^a^g^a^g^c^T(Y)^T(Y)^g | 10 |
| hAr14c-1065-AmNA(15) (ASO-1065) | G(Y)^G(Y)^T(Y)^a^a^a^t^c^a^g^a^c^T(Y)^T(Y)^c | 11 |
| hAr14c-1246-AmNA(15) | G(Y)^G(Y)^A(Y)^g^t^g^g^g^a^a^g^a^A(Y)^A(Y)^t | 12 |
| hAr14c-1316-AmNA(15) (ASO-1316) | G(Y)^5(Y)^A(Y)^t^a^c^c^t^c^a^g^g^T(Y)^A(Y)^a | 13 |
| hAr14c-1454-AmNA(15) (ASO-1454) | A(Y)^G(Y)^G(Y)^a^c^a^a^a^t^g^a^a^A(Y)^T(Y)^t | 14 |
| hAr14c-1710-AmNA(15) | T(Y)^T(Y)^T(Y)^t^t^t^t^a^t^t^t^t^T(Y)^A(Y)^t | 15 |
| hAr14c-1819-AmNA(15) | 5(Y)^5(Y)^A(Y)^g^c^a^t^t^t^a^c^a^5(Y)^5(Y)^a | 16 |
| hAr14c-1977-AmNA(15) | G(Y)^5(Y)^A(Y)^a^t^t^c^a^g^c^a^c^A(Y)^5(Y)^a | 17 |
| hAr14c-2055-AmNA(15) | 5(Y)^A(Y)^T(Y)^c^a^t^g^t^c^t^g^a^A(Y)^A(Y)^a | 18 |
| hAr14c-2082-AmNA(15) | T(Y)^A(Y)^T(Y)^t^c^a^t^t^t^g^t^a^A(Y)^A(Y)^a | 19 |
| hAr14c-2146-AmNA(15) | 5(Y)^A(Y)^T(Y)^a^a^a^g^g^a^a^t^a^T(Y)^A(Y)^a | 20 |
| hAr14c-2220-AmNA(15) | T(Y)^T(Y)^T(Y)^t^t^a^a^t^g^a^a^a^G(Y)^A(Y)^c | 21 |
| hAr14c-2264-AmNA(15) | G(Y)^T(Y)^T(Y)^t^t^a^t^t^t^t^t^t^T(Y)^G(Y)^g | 22 |
| hAr14c-2314-AmNA(15) | 5(Y)^5(Y)^T(Y)^t^c^t^c^t^t^t^t^a^A(Y)^T(Y)^t | 23 |
| hAr14c-2448-AmNA(15) | 5(Y)^T(Y)^G(Y)^a^g^t^a^c^c^a^g^t^G(Y)^A(Y)^c | 24 |
| hAr14c-2555-AmNA(15) | A(Y)^T(Y)^T(Y)^a^t^a^a^a^g^g^a^t^T(Y)^T(Y)^t | 25 |
| hAr14c-2715-AmNA(15) | T(Y)^T(Y)^G(Y)^t^a^a^a^g^a^a^a^t^G(Y)^T(Y)^g | 26 |
| hAr14c-2773-AmNA(15) | A(Y)^T(Y)^A(Y)^a^t^t^t^g^a^c^t^a^A(Y)^5(Y)^t | 27 |
| hAr14c-2781-AmNA(15) | A(Y)^G(Y)^G(Y)^g^a^c^t^c^a^t^a^a^T(Y)^T(Y)^t | 28 |
| hAr14c-2850-AmNA(15) | T(Y)^5(Y)^A(Y)^a^g^c^a^g^g^a^a^g^5(Y)^5(Y)^a | 29 |
| hAr14c-2936-AmNA(15) | G(Y)^G(Y)^G(Y)^g^t^a^c^c^a^a^a^t^A(Y)^5(Y)^a | 30 |
| hAr14c-2970-AmNA(15) | T(Y)^5(Y)^T(Y)^a^c^t^g^a^g^t^t^t^(5Y)^T(Y)^a | 31 |
| hAr14c-3071-AmNA(15) | 5(Y)^T(Y)^T(Y)^c^a^g^a^t^g^a^t^g^G(Y)^G(Y)^a | 32 |
| hAr14c-3105-AmNA(15) | G(Y)^A(Y)^T(Y)^g^g^a^t^t^t^t^t^t^T(Y)^T(Y)^t | 33 |
| hAr14c-3187-AmNA(15) | A(Y)^T(Y)^A(Y)^t^a^t^t^t^a^t^t^c^t^5(Y)^T(Y)^c | 34 |
| hAr14c-3225-AmNA(15) (ASO-3225) | A(Y)^G(Y)^G(Y)^t^t^a^c^a^g^t^a^t^T(Y)^T(Y)^g | 35 |
| hAr14c-3245-AmNA(15) | T(Y)^A(Y)^A(Y)^g^t^a^t^t^g^t^t^a^T(Y)^5(Y)^a | 36 |
| hAr14c-3332-AmNA(15) | G(Y)^5(Y)^A(Y)^c^c^c^t^t^a^a^g^t^A(Y)^T(Y)^t | 37 |
| hAr14c-3378-AmNA(15) | T(Y)^A(Y)^5(Y)^a^c^c^a^c^a^g^g^g^5(Y)^T(Y)^t | 38 |

TABLE 1-continued

| Sequence Name (Number of Bases) | Sequence (5'→3') | SEQ ID NO |
|---|---|---|
| hAr14c-3431-AmNA(15) | A(Y)^T(Y)^T(Y)^a^t^t^a^g^g^t^c^a^A(Y)^A(Y)^c | 39 |
| hAr14c-3597-AmNA(15) | G(Y)^A(Y)^G(Y)^g^g^a^g^g^c^c^a^a^5(Y)^T(Y)^t | 40 |
| hAr14c-3649-AmNA(15) | G(Y)^A(Y)^A(Y)^a^c^a^g^a^a^c^t^g^G(Y)^5(Y)^c | 41 |
| hAr14c-3728-AmNA(15) | A(Y)^5(Y)^A(y)^g^c^a^g^t^a^g^a^a^A(Y)^G(Y)^g | 42 |
| hAr14c-3756-AmNA(15) | A(Y)^A(Y)^A(Y)^g^a^g^a^a^g^g^a^t^G(Y)^A(Y)^t | 43 |
| hAr14c-3822-AmNA(15) | T(Y)^G(Y)^A(Y)^t^t^g^t^a^t^a^a^a^T(Y)^A(Y)^a | 44 |
| hAr14c-3223-AmNA(17) | A(Y)^G(Y)G(Y)^t^t^a^c^a^g^t^a^t^t^t^G(Y)^G(Y)^c | 45 |
| hAr14c-3221-AmNA(19) | A(Y)^G(Y)^G(Y)^t^t^a^c^a^g^t^a^t^t^t^g^g^5(Y)^A(Y)^t | 46 |
| hAr14c-3223-AmNA(15) | G(Y)^T(Y)^T(Y)^a^c^a^g^t^a^t^t^t^G(Y)^G(Y)^c | 47 |
| hAr14c-3221-AmNA(17) | G(Y)^T(Y)^T(Y)^a^c^a^g^t^a^t^t^t^g^g^5(Y)^A(Y)^t | 48 |
| hAr14c-3219-AmNA(19) | G(Y)^T(Y)^T(Y)^a^c^a^g^t^a^t^t^t^g^g^c^a^T(Y)^5(Y)^t | 49 |
| hAr14c-3221-AmNA(15) | T(Y)^A(Y)^5(Y)^a^g^t^a^t^t^t^g^g^5(Y)^A(Y)^t | 50 |
| hAr14c-3219-AmNA(17) | T(Y)^A(Y)^5(Y)^a^g^t^a^t^t^t^g^g^c^a^T(Y)^5(Y)^t | 51 |
| hAr14c-3217-AmNA(19) | T(Y)^A(Y)^5(Y)^a^g^t^a^t^t^t^g^g^c^a^t^c^T(Y)^G(Y)^c | 52 |
| hAr14c-3227-AmNA(15) | G(Y)^A(Y)^A(Y)^g^g^t^t^a^c^a^g^t^A(Y)^T(Y)^t | 53 |
| hAr14c-3225-AmNA(17) | G(Y)^A(Y)^A(Y)^g^g^t^t^a^c^a^g^t^a^t^T(Y)^T(Y)^g | 54 |
| hAr14c-3223-AmNA(19) (ASO-3223) | G(Y)^A(Y)^A(Y)^g^g^t^t^a^c^a^g^t^a^t^t^t^G(Y)^G(Y)^c | 55 |
| hAr14c-3229-AmNA(15) | G(Y)^A(Y)^G(Y)^a^a^g^g^t^t^a^c^a^G(Y)^T(Y)^a | 56 |
| hAr14c-3227-AmNA(17) | G(Y)^A(Y)^G(Y)^a^a^g^g^t^t^a^c^a^g^t^A(Y)^T(Y)^t | 57 |
| hAr14c-3225-AmNA(19) | G(Y)^A(Y)^G(Y)^a^a^g^g^t^t^a^c^a^g^t^a^t^T(Y)^T(Y)^g | 58 |
| hAr14c-1314-AmNA(17) | G(Y)^5(Y)^A(Y)^t^a^c^c^t^c^a^g^g^t^a^A(Y)^T(Y)^t | 59 |
| hAr14c-1312-AmNA(19) (ASO-1312) | G(Y)^5(Y)^A(Y)^t^a^c^c^t^c^a^g^g^t^a^a^t^T(Y)^5(Y)^a | 60 |
| hAr14c-1318-AmNA(15) | A(Y)^T(Y)^G(Y)^c^a^t^a^c^c^t^c^a^G(Y)^G(Y)^t | 61 |
| hAr14c-1316-AmNA(17) | A(Y)^T(Y)^G(Y)^c^a^t^a^c^c^t^c^a^g^g^T(Y)^A(Y)^a | 62 |
| hAr14c-1314-AmNA(19) | A(Y)^T(Y)^G(Y)^c^a^t^a^c^c^t^c^a^g^g^t^a^A(Y)^T(Y)^t | 63 |
| hAr14c-1320-AmNA(15) | A(Y)^A(Y)^A(Y)^t^g^c^a^t^a^c^c^t^5(Y)^A(Y)^g | 64 |
| hAr14c-1318-AmNA(17) | A(Y)^A(Y)^A(Y)^t^g^c^a^t^a^c^c^t^c^a^G(Y)^G(Y)^t | 65 |
| hAr14c-1316-AmNA(19) | A(Y)^A(Y)^A(Y)^t^g^c^a^t^a^c^c^t^c^a^g^g^T(Y)^A(Y)^a | 66 |
| hAr14c-1314-AmNA(15) | A(Y)^T(Y)^A(Y)^c^c^t^c^a^g^g^t^a^A(Y)^T(Y)^t | 67 |
| hAr14c-1312-AmNA(17) | A(Y)^T(Y)^A(Y)^c^c^t^c^a^g^g^t^a^a^t^T(Y)^5(Y)^a | 68 |
| hAr14c-1310-AmNA(19) | A(Y)^T(Y)^A(Y)^c^c^t^c^a^g^g^t^a^a^t^t^c^A(Y)^5(Y)^a | 69 |
| hAr14c-1312-AmNA(15) | A(Y)^5(Y)^5(Y)^t^c^a^g^g^t^a^a^t^T(Y)^5(Y)^a | 70 |
| hAr14c-1310-AmNA(17) | A(Y)^5(Y)^5(Y)^t^c^a^g^g^t^a^a^t^t^c^A(Y)^5(Y)^a | 71 |

TABLE 1-continued

| Sequence Name (Number of Bases) | Sequence (5'→3') | SEQ ID NO |
|---|---|---|
| hAr14c-1308-AmNA(19) | A(Y)^5(Y)^5(Y)^t^c^a^g^g^t^a^a^t^t^c^a^c^A(Y)^G(Y)^g | 72 |
| hAr14c-1452-AmNA(17) | A(Y)^G(Y)^G(Y)^a^c^a^a^a^t^g^a^a^a^t^T(Y)^T(Y)^c | 73 |
| hAr14c-1450-AmNA(19) (ASO-1450) | A(Y)^G(Y)^G(Y)^a^c^a^a^a^t^g^a^a^a^t^t^t^5(Y)^A(Y)^a | 74 |
| hAr14c-1452-AmNA(15) | G(Y)^A(Y)^5(Y)^a^a^a^t^g^a^a^a^t^T(Y)^T(Y)^c | 75 |
| hAr14c-1450-AmNA(17) | G(Y)^A(Y)^5(Y)^a^a^a^t^g^a^a^a^t^t^t^5(Y)^A(Y)^a | 76 |
| hAr14c-1448-AmNA(19) | G(Y)^A(Y)^5(Y)^a^a^a^t^g^a^a^a^t^t^t^c^a^A(Y)^5(Y)^a | 77 |
| hAr14c-1450-AmNA(15) | 5(Y)^A(Y)^A(Y)^a^t^g^a^a^a^t^t^t^5(Y)^A(Y)^a | 78 |
| hAr14c-1448-AmNA(17) | 5(Y)^A(Y)^A(Y)^a^t^g^a^a^a^t^t^t^c^a^A(Y)^5(Y)^a | 79 |
| hAr14c-1446-AmNA(19) | 5(Y)^A(Y)^A(Y)^a^t^g^a^a^a^t^t^t^c^a^a^c^A(Y)^G(Y)^g | 80 |
| hAr14c-1456-AmNA(15) | G(Y)^5(Y)^A(Y)^g^g^a^c^a^a^a^t^g^A(Y)^A(Y)^a | 81 |
| hAr14c-1454-AmNA(17) | G(Y)^5(Y)^A(Y)^g^g^a^c^a^a^a^t^g^a^a^A(Y)^T(Y)^t | 82 |
| hAr14c-1452-AmNA(19) | G(Y)^5(Y)^A(Y)^g^g^a^c^a^a^a^t^g^a^a^a^t^T(Y)^T(Y)^c | 83 |
| hAr14c-1458-AmNA(15) | G(Y)^A(Y)^G(Y)^c^a^g^g^a^c^a^a^a^T(Y)^G(Y)^a | 84 |
| hAr14c-1456-AmNA(17) | G(Y)^A(Y)^G(Y)^c^a^g^g^a^c^a^a^a^t^g^A(Y)^A(Y)^a | 85 |
| hAr14c-1454-AmNA(19) | G(Y)^A(Y)^G(Y)^c^a^g^g^a^c^a^a^a^t^g^a^a^A(Y)^T(Y)^t | 86 |

In Table, "G(Y)" represents guanine having a structure of AmNA (2',4'-bridged nucleotide in which R is a methyl group in General Formula (1) described above),
"A(Y)" represents adenine having a structure of AmNA,
"T(Y)" represents thymine having a structure of AmNA,
"5(Y)" represents 5-methylcytosine having a structure of AmNA, and
"^" represents a phosphorothioate bond.

HLE cells, HCT116 cells, and A549 cells were transfected with 25 to 50 nM ASO and 10 to 20 nM siRNA using Lipofectamine 3000 (Invitrogen, Carlsbad, CA, USA) or RNAiMAX (Invitrogen). Transfected cells were used in the experiments 36 to 48 hours after the end of the transfection.

1-5. Xenograft Liver Tumor Formation and Treatment with ASO In Vivo

Pellets of HLE cells (1×10$^7$ cells) were suspended in 100 µl of Matrigel matrix high concentration (BD Biosciences, San Jose, CA, USA) and were injected into the livers of 8-week-old male nude mice (BALB/cAJcl-nu/nu, CLEA Japan, Inc.) under anesthesia (day 0). From day 0, ASO (50 µg/body; about 2.5 mg/kg) was subcutaneously administered twice a week. Mice were euthanized 29 days after the HLE cell transplantation, and tumors were recovered and subjected to histological analysis.

HCT116/Luc cells (2.5×10$^5$ cells) were suspended in 100 µl of phosphate buffer solution (PBS), and were injected into the spleens of 8-week-old male nude mice (BALB/cAJcl-nu/nu, CLEA Japan, Inc.) under anesthesia. After 19 days had elapsed since the transplantation, ASO (50 µg/body; about 2.5 mg/kg) was subcutaneously administered twice a week. Mice were euthanized 47 days after the HCT116/Luc cell transplantation and were subjected to histological analysis.

Tumor growth analysis was performed by recording bioluminescence images at a frequency of once a week, in the following manner: VivoGlo luciferin (30 mg/ml) was administered intraperitoneally, and 10 minutes after the administration of VivoGlo luciferin, recording was carried out using an IVIS imaging system (Xenogen Corp., Alameda, CA, USA).

1-6. Clinical Data Analysis Using Open Source

ARL4C mRNA expression data regarding the livers of liver cancer patients and colorectal cancer patients were obtained from the Gene Expression Profiling Interactive Analysis (GEPIA) online database (http://gepia.cancer-pku.cn/). Tumor samples and normal samples in the GEPIA database were obtained from the Cancer Genome Atlas (TCGA) project and the Genotype-Tissue Expression (GTEx) project. Expression difference analysis was performed by one-way analysis of variance (one-way ANOVA). A p-value of less than 0.05 was determined to be statistically significant. The correlation of the overall survival rate with ARL4C mRNA expression in colorectal cancers in the TCGA dataset was analyzed using OncoLnc (http://www.oncolnc.org), and was visualized by using GraphPad Prism (GraphPad Software, San Diego, CA). The ARL4C high expression group and the ARL4C low expression group were designated according to the median value of the ARL4C expression in colorectal cancer patients in the dataset. Co-expression analysis using the TCGA dataset was performed using the R2: Genomics Analysis Platform (http://r2.amc.nl) and visualized using GraphPad Prism. The p-value and the r-value were calculated using GraphPad Prism.

1-7. Identification of Potential Off-Target Genes for ARL4C ASOs by in Silico Analysis of Candidate Genes Potential off-target genes in ARL4C ASO (hARL4C ASO-1316-AmNA [15-mer] (ARL4C ASO-1316) and hARL4C-3223-AmNA [19-mer] (ARL4C ASO-3223)) were identified by using database "Human Genomic plus Transcript (Human G+T)" (Build 2.7.1) as well as basic local alignment search tools (BLAST+programs) using Mega-Blast algorithm.

1-8. Formation of Xenograft Orthotopic Transplantation Model Using Lung Cancer Cells and Treatment with ASO In Vivo Eight-week-old male nude mice (BALB/cAJcl-nu/nu, CLEA Japan, Inc.) were intraperitoneally injected with medetomidine (0.75 mg/kg), midazolam (4 mg/kg), and butorphanol (5 mg/kg) so as to be anesthetized. The xenograft orthotopic transplantation model was formed by transplanting human lung cancer cells into the left lungs of mice in the following order. A549/Luc cells (approximately $2 \times 10^6$ cells) were suspended in 10 μl of PBS (phosphate buffered saline) and 10 μl of Matrigel (BD Biosciences, San Jose, CA, USA), and a 29 G needle attached to a 0.5 ml insulin syringe (BD Biosciences, San Jose, CA, USA) was used to inject the same through the intercostal space to a depth of 2 mm in the left lung. The incision in the skin was closed with a 5-0 polypropylene suture, and the mice were rested on a warm carpet until they were fully recovered.

One week after the tumor transplantation, tumor establishment was confirmed using an IVIS imaging system (Xenogen Corp., Alameda, CA, USA). In the in-vivo imaging, 100 μl of VivoGlo luciferin (30 mg/ml) was administered via the tail vein, and bioluminescence imaging was recorded 5 minutes after the administration. Mice with established tumors were then divided into two groups, a control ASO inhalation group (n=7) and an ARL4C ASO inhalation group (n=9) in such a manner that the groups had identical IVIS signal intensities. When 7, 11 and 15 days elapsed after the tumor transplantation, ASO (200 μg/body, about 10 mg/kg) dissolved in 25 μl was administered transbronchially using a 22 G intravenous catheter, according to the procedure reported by Kim M P et al. (Nat Protoc 2009; 4: 1670-80). When 21 days elapsed after the tumor transplantation, tumor sizes were determined using the IVIS imaging system, and then the mice were euthanized for histological analysis. All protocols in this study were carried out under the approval of the Animal Experiment Committee of Osaka University (No. 26-032-048).

1-9. Formation of Xenograft Orthotopic Transplantation Model Using Pancreatic Cancer Cells and Treatment with ASO in Vivo Assay based on the xenograft orthotopic transplantation model using pancreatic cancer cells was performed by arranging the method described in the literature (Kim M P. et. al., Nat Protoc 2009; 4: 1670-80). Specifically, S2-CP8/Luc cells ($5 \times 10^5$ cells) were suspended in 100 μl of Hanks' Balanced Salt Solution (HBSS) containing 50% matrigel, and were orthotopically transplanted in the central part of the pancreas using a 27 G needle. Three days after transplantation, the mice were divided into two groups, a control ASO-administered group (n=6) and an ARL4C ASO-administered group (n=7). After three days had elapsed since the transplantation, ASO (50 μg/body, approximately 2.5 mg/kg) was subcutaneously administered twice a week. Tumors were quantified once a week using the IVIS imaging system (Xenogen Corp.). In the in-vivo imaging, 100 μl of VivoGlo luciferin (30 mg/ml) was intraperitoneally administered, and bioluminescence images were recorded eight minutes after the administration. The quantification of the tumors was carried out in the following manner: a region of interest (ROI) was selected, and a radiance value of the same was measured using Living Image 4.3.1 Software (Caliper Life Science). The mice were euthanized 28 days after the transplantation, tumor weights and the number of mesenteric lymph nodes (lymph nodes of 1 mm or larger in diameter) were determined, and histological analysis was carried out. All protocols in this study were carried out under the approval of the Animal Experiment Committee of Osaka University (No. 26-032-048).

1-10. Statistical Analysis

Each experiment was performed at least 3 times; the results are expressed as mean t standard deviation (s.d.). The cumulative probability of recurrence-free survival rate was determined using the Kaplan-Meier method. Statistical significance differences were determined using the log rank test. Statistical significance differences in other experiments were determined by the Student's t-test. With a p-value of less than 0.05, it was determined that there was a statistically significant difference.

1-11. Other Test Methods and Test Materials

Cell migration assays and quantitative real-time PCR analyses were performed according to the methods reported by Fujii S et al. (Oncogene 2015; 34: 4834-44).

Primers and siRNAs used in the experiments are as shown in Tables 2 and 3.

TABLE 2

Primer

| Primer | Sequence |
| --- | --- |
| human ARLAC | AGGGGCTGTGAAGCTGAGTA (SEQ ID NO: 87) TTCCAGGCTGAAAAGCAGTT (SEQ ID NO: 88) |
| human CTNNB1 | GAAACGGCTTTCAGTTGAGC (SEQ ID NO: 89) CTGGCCATATCCACCAGAGT (SEQ ID NO: 90) |
| human PIK3CD | TGGAATTCTGGACCAAGGAG (SEQ ID NO: 91) AAAGTTGGGGGAGTTCTCGT (SEQ ID NO: 92) |
| human NLN | GCTGAACTTGGTGCTCTTCC (SEQ ID NO: 93) TAGTTTGGCCACCTTGGTTC (SEQ ID NO: 94) |
| human FBXL9 | AGCTGTGTGCCTCTTGTGTG (SEQ ID NO: 95) AGTTGGGGATCTCTGCATTG (SEQ ID NO: 96) |
| human GARDH | TCCTGCACCACCAACTGCTT (SEQ ID NO: 97) TGGCAGTGATGGCATGGAC (SEQ ID NO: 98) |

TABLE 3 siRNA

| Target genes | Target Sequences |
| --- | --- |
| Randomized control | CAGTCGCGTTTGCGACTGG (SEQ ID NO: 99) |

TABLE 3-continued

| Target genes | siRNA Target Sequences |
|---|---|
| human Cmnb1 | CCCACTAATGTCCAGCGTT (#1, for open reading frame) (SEQ ID NO: 100) GCATAACCTTTCCCATCAT (#2, for open reading frame) (SEQ ID NO: 101) |
| human PIK3CD | GCGAATACTCTGCCATTAT (#1, for 3'-untranslated region) (SEQ ID NO: 102) GCCAACTAACTCTGCAGAT (#2, for 3'-untranslated region) (SEQ ID NO: 103) |

In Table, each siRNA indicates the base sequence of the sense strand.

The cell proliferation assays were performed using the CyQUANT NF Cell Proliferation Assay Kits (Thermo Fisher Scientific), in the way recommended by the manufacturer.

Fluorescence was measured using a fluorescence microplate reader (Synergy™ HTX Multi-Mode Microplate Reader, BioTek, Winooski, VT, USA).

2. Test Results 2-1. Expression of ARL4C in Primary and Metastatic Cancers

The expression of ARL4C in primary liver cancers was analyzed immunohistochemically. Tumors with more than 20% of tumor cells stained with an anti-ARL4C antibody were determined to be ARL4C positive. Of the 128 liver cancer cases, 33 (25.8%) were ARL4C positive. An ARL4C-positive primary liver cancer was immunostained with the anti-ARL4C antibody, and the image is shown in (a) of FIG. 1. In the ARL4C-positive primary liver cancer, almost no expression of ARL4C was observed in a non-tumor area.

Figure 2:
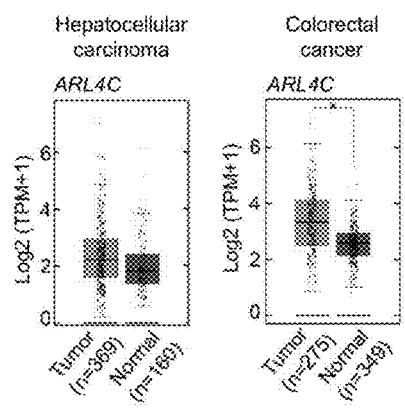
FIG. 2 shows the results obtained by analyzing ARL4C mRNA amounts in liver cancers and normal livers, as well as in rectal cancers and normal rectums, using the TCGA dataset.

The relationship between the expression of ARL4C and clinicopathological factors in liver cancer patients was analyzed, and the results thereof are shown Table 4. Analysis using a dataset (Gene Expression Profiling Interactive Analysis; GEPIA) combining Cancer Genome Atlas (TCGA) and Genotype-Tissue Expression (GTEx) shows that the ARL4C mRNA amount in liver cancers was not statistically significantly higher than that in normal liver cells. However, as shown in FIG. 2, the ARL4C mRNA amount in liver cancers tended to be higher than that in normal livers. It was also found that ARL4C positivity was associated with vascular infiltration (P=0.02).

TABLE 4

| Liver Cancer Patient | | | |
|---|---|---|---|
| | ARL4C negative (n = 95) | ARL4C positive (n = 33) | P value |
| General Background | | | |
| Age (Year) | 68 (21-81) | 69 (50-81) | 0.15 |
| Sex (Male/Female) | 83/12 | 31/2 | 0.30 |
| Hepatitis Virus Infection (HB or HC/non-B and non-C)[#1] | 54/41 | 21/12 | 0.49 |
| Child-Pugh Score (A/B) | 94/1 | 31/2 | 0.10 |
| Tumor Factor | | | |
| Number of Tumors (>2/1) | 37/58 | 18/15 | 0.12 |
| Tumor Size (≥5 cm/<5 cm) | 43/52 | 17/16 | 0.54 |
| Tissue Type (well or moderate/poor) | 74/20 | 22/11 | 0.17 |
| Lymph Node Metastasis (negative/positive) | 95/0 | 32/1 | 0.09 |
| Vascular Infiltration (negative/positive) | 65/30 | 15/18 | 0.02 |
| Membrane Formation (negative/positive) | 16/79 | 3/30 | 0.28 |
| Membrane Infiltration (negative/positive) | 34/61 | 7/26 | 0.12 |
| Stage (I-II/IIIA-IVA) | 65/30 | 18/15 | 0.15 |

[#1]HB, Hepatitis B; HC, Hepatitis C; non-B and non-C, Non-Hepatitis B and Non-Hepatitis C A univariate analysis of the recurrence-free survival rate in liver cancer patients was carried out using the Cox proportional hazard model; the results thereof are shown in Table 5. The results of the univariate analysis show that the gender, the tumor count>2, the poorly differentiated type, the lymph node metastasis, the vascular infiltration, Stages IIIA to IVA, and the ARL4C expression correlated with a decrease in the disease-free survival.

TABLE 5

| Liver Cancer Patient | | | | |
|---|---|---|---|---|
| | Number | Hazard Ratio | 95% CI | P value |
| Age (≥65 years/<65 years) | 87/41 | 1.31 | 0.81-2.20 | 0.27 |
| Sex (Male/Female) | 114/14 | 0.45 | 0.25-0.91 | 0.028 |
| Hepatitis Virus Infection (HB or HC/non-B and non-C) | 75/53 | 1.22 | 0.78-1.95 | 0.38 |
| Child-Pugh Score (B/A) | 3/125 | 5.10 | 1.23-14.15 | 0.029 |
| Number of Tumors (>2/1) | 55/73 | 2.64 | 1.68-4.17 | <0.0001 |
| Tumor Size (≥5 cm/<5 cm) | 60/68 | 1.49 | 0.96-2.34 | 0.078 |
| Tissue Type (poor/well or moderate) | 31/96 | 1.96 | 1.18-3.16 | 0.010 |

TABLE 5-continued

| Liver Cancer Patient | Number | Hazard Ratio | 95% CI | P value |
|---|---|---|---|---|
| Lymph Node Metastasis (positive/negative) | 1/127 | 31.35 | 1.60-211.89 | 0.030 |
| Vascular Infiltration (positive/negative) | 48/80 | 2.61 | 1.66-4.09 | <0.0001 |
| Membrane Formation (positive/negative) | 109/19 | 0.89 | 0.52-1.66 | 0.70 |
| Membrane Infiltration (positive/negative) | 87/41 | 1.19 | 0.74-1.94 | 0.48 |
| Stage (IIIA-IVA/I-II) | 83/45 | 2.43 | 1.54-3.80 | 0.0002 |
| ARL4C expression (positive/negative) | 33/95 | 1.68 | 1.02-2.69 | 0.042 |

A multivariate analysis of the recurrence-free survival rate in patients with Stage 0 to IIIC liver cancers was carried out using the Cox proportional hazard model; the results thereof are shown in Table 6. The results of a multivariate analysis reveal that the tumor count>2 was an independent prognostic factor (P=0.0003). Furthermore, the results also reveal that the ARL4C positivity tended to be independently associated with a poor prognosis (P=0.066). In addition, the relationship between the recurrence-free survival rate and the ARL4C expression in liver cancer patients was analyzed; the results thereof are shown in (b) of FIG. 1. From these results, it was found that the recurrence-free survival rate significantly decreased in ARL4C-positive liver cancer patients (P=0.0328). These results suggest that the ARL4C expression correlates with liver cancer activities.

TABLE 6

| Liver Cancer Patient | Number | Hazard Ratio | 95% | P value |
|---|---|---|---|---|
| Sex (Male/Female) | 114/14 | 0.54 | 0.28-1.12 | 0.093 |
| Number of Tumors (>2/1) | 55/73 | 2.37 | 1.50-3.79 | 0.0003 |
| Tissue Type (poor/well or moderate) | 31/96 | 1.57 | 0.93-2.59 | 0.09 |
| ARL4C expression (positive/negative) | 33/95 | 1.62 | 0.97-2.66 | 0.066 |

The relationship between the expression of ARL4C and clinicopathological factors in colorectal cancer patients was analyzed; the results thereof are shown in Table 7. In the 102 patients with Stage 0 to IIIC colorectal cancers, 24.5% of the tumors were confirmed to be ARL4C positive. It was also found that the ARL4C positivity correlated with the tumor infiltration, the vascular infiltration, and Stages IIA to IIIC.

TABLE 7

| Colorectal Cancer Patient | ARL4C negative (n = 77) | ARL4C positive (n =25) | P value |
|---|---|---|---|
| General Background | | | |
| Age (Year) | 69 (39-91) | 65 (28-85) | 0.06 |
| Sex (Male/Female) | 48/29 | 15/10 | 0.83 |
| Tumor Factor | | | |
| Tissue Type (well or moderate or mucinous/poor) | 74/3 | 23/2 | 0.59 |
| Tumor Infiltration (M or SM/MP-SI)[#1)] | 33/44 | 4/21 | 0.017 |
| Vascular Infiltration (negative/positive) | 57/19 | 12/13 | 0.024 |
| Lymph Infiltration (negative/positive) | 33/43 | 8/17 | 0.36 |
| Lymph Node Metastasis (negative/positive) | 51/26 | 17/8 | 1.00 |
| Stage (0-I/IIA-IIIC) | 42/35 | 6/19 | 0.011 |

[#1)]M, Mucous Membrane; SM, Submucosal Layer; MP, Muscularis Propria; SI, invasion of adjacent structures A univariate analysis of recurrence-free survival rate in colorectal cancer patients was carried out using the Cox proportional hazard model; the results thereof are shown in Table 8. The results of the univariate analysis reveal that the depth of tumor infiltration beyond the submucosal layer, the vascular infiltration, the lymphatic infiltration, the lymph node metastasis, Stages II to IIIC, and the ARL4C expression were associated with the decrease in the recurrence-free survival rate.

TABLE 8

| Colorectal Cancer Patient | Number | Hazard Ratio | 95% CI | P value |
|---|---|---|---|---|
| Age (≥65 years/<65 years) | 63/39 | 1.47 | 0.65-3.30 | 0.35 |
| Sex (Male/Female) | 63/39 | 2.00 | 0.84-5.51 | 0.12 |
| Tissue Type (poor/well, moderate or mucinous) | 5/97 | 1.9 × 109 | 1.86 | 0.15 |
| Tumor Infiltration (MP-SI/M or SM) | 65/37 | 8.6 × 109 | 8.30 | <0.0001 |
| Vascular Infiltration (positive/negative) | 32/69 | 7.72 | 3.32-20.04 | <0.0001 |
| Lymph Infiltration (positive/negative) | 60/41 | 5.60 | 1.93-23.72 | 0.0007 |
| Lymph Node Metastasis (positive/negative) | 34/68 | 2.93 | 1.31-6.69 | 0.01 |
| Stage (IIA-IIIC/0-I) | 64/48 | 12.87 | 3.79-80.37 | <0.0001 |
| ARL4C expression (positive/negative) | 25/77 | 4.79 | 2.14-11.12 | 0.0002 |

A multivariate analysis of recurrence-free survival rate in patients with Stage 0 to IIIC colorectal cancers was carried out using the Cox proportional hazard model; the results thereof are shown in Table 9. The results show that the expression of ARL4C was an independent prognostic factor in colorectal cancers. In addition, the relationship between the recurrence-free survival rate and the ARL4C expression in colorectal cancer patients was analyzed; the results thereof are shown in (c) of FIG. 1. From the results, it was also confirmed that ARL4C-positive colorectal cancer patients had significantly reduced recurrence-free survival rates (P<0.0001).

TABLE 9

| Colorectal Cancer Patient | Number | Hazard Ratio | 95% CI | P value |
|---|---|---|---|---|
| Lymph Infiltration (positive/negative) | 60/41 | 3.29 | 0.94-15.17 | 0.063 |
| Lymph Node Metastasis (positive/negative) | 34/68 | 1.93 | 0.80-4.96 | 0.14 |
| ARL4C expression (positive/negative) | 25/77 | 4.51 | 1.98-10.61 | 0.0004 |

In addition, the relationship between ARL4C expression and overall survival rates was analyzed using the Cancer Genome Atlas (TCGA) dataset on colorectal cancer patients; the results are shown in (d) of FIG. 1. From the results of the analysis using the TCGA dataset, it was also confirmed that the ARL4C high expression group had a lower recurrence-free survival rate as compared with the ARL4C low expression group.

Regarding tumors resulting from metastasis of colorectal cancers to the livers (24 cases), the ARL4C expression was measured immunohistologically; the results are shown in (e) of FIG. 1. The 24 cases included 11 cases of recurrent liver metastasis (metachronous liver metastasis) after excision of colorectal cancers, and 13 cases of colorectal cancers accompanied by liver metastasis (synchronous liver metastasis). In cases of metachronous liver metastasis, ARL4C was expressed in 11 cases of colon tumors (100%) and 9 cases of liver tumors (81.8%) ((e) of FIG. 1). Also, in all of the cases, ARL4C was detected minimally in the non-tumor areas. Thus, it was found that, as described above, the ARL4C expression in a colorectal cancer was associated with a poor prognosis, and that an increase in the ARL4C expression level was observed in colorectal cancer cases with liver metastasis.

2-2. Screening of ARL4C ASOs and Influence of ARL4C ASOs on Proliferation and Migration of Liver Cancer Cells and Colorectal Cancer Cells First, base sequences of 15-nucleotide ARL4C were selected based on the structure of ARL4C mRNA. From thousands of ARL4C ASO candidates, those that may cause hepatotoxicity were excluded, and 38 types of ARL4C ASOs (those other than ASO-1312, ASO-1450 and ASO-3223 among the ASOs in Table 1) were selected, by high-dimensional structure prediction of ARL4C mRNA. The ASOs used in this test were those in which all of the phosphodiester bonds were substituted with phosphorothioate bonds. Knockdown efficiencies of ARL4C ASOs in A549 cells (lung adenocarcinoma cells) were investigated by screening experiments using real-time PCR. It has been confirmed that the protein abundance of ARL4C in A549 cells is reduced by treatment with ARL4C siRNA. The ARL4C mRNA amounts in A549 cells treated with 38 types of ARL4C ASOs were measured, and the results are shown in (a) of FIG. 3. Of the 38 types of ARL4C ASOs, 7 types of ARL4C ASOs having high knockdown efficiencies (ASO-650, ASO-793, ASO-986, ASO-1065, ASO-1316, ASO-1454, and ASO-3225) were selected for further analysis.

Figure 3:
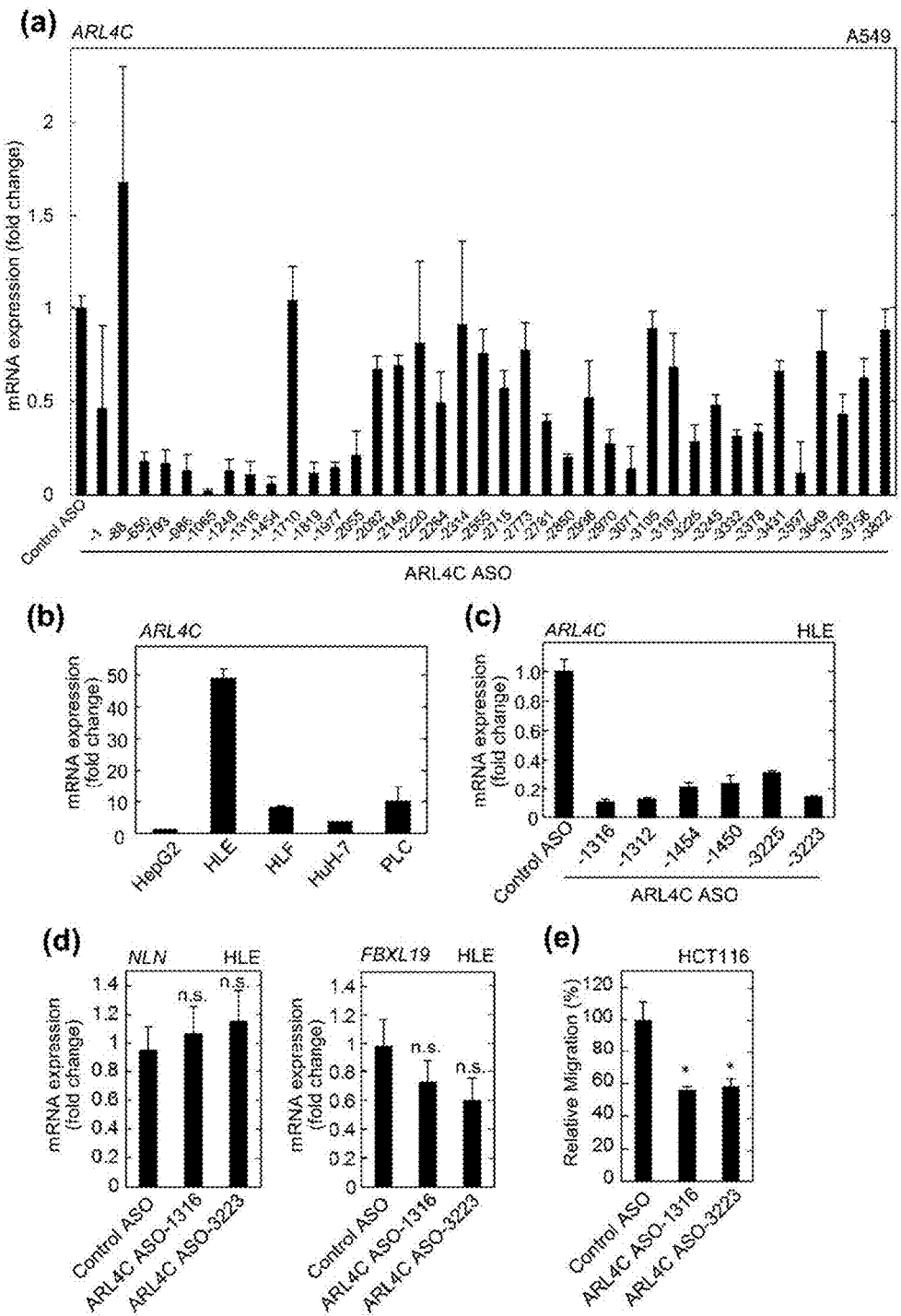
FIG. 3 (a) shows the results obtained by measuring ARL4C mRNA amounts in A549 cells treated with 38 types of ARL4C ASOs. (b) shows the results obtained by measuring ARL4C mRNA amounts in 5 types of liver cancer cells (HepG2, HLE, HLF, HuH-7, and PLC). (c) shows the results obtained by transfecting HLE cells with ARL4C ASOs (ASO-1316, ASO-1312, ASO-1454, ASO-1450, ASO-3225, and ASO-3223) at 25 nM each and measuring ARL4C mRNA amounts by real-time PCR. (d) shows the results obtained by transfecting HLE cells with ASO-1316 and ASO-3223 at 25 nM each and measuring mRNA amounts of neurolysin (NLN) and sapiens F-box and leucine-rich repeat protein 19 (FBXL19) by real-time PCR. (e) shows the results obtained by transfecting HCT116 cells with ASO-1316 and ASO-3223 at 25 nM each and performing a cell migration assay.

The ARL4C mRNA amounts in 5 types of liver cancer cells (HLE, HLF, PLC, HuH-7 cells, and HepG2) were measured, and the results thereof are shown in (b) of FIG. 3. As can be seen from (b) of FIG. 3, the HLE cells had the highest ARL4C mRNA amount, and the HepG2 cells hardly expressed ARL4C mRNA.

Figure 4:
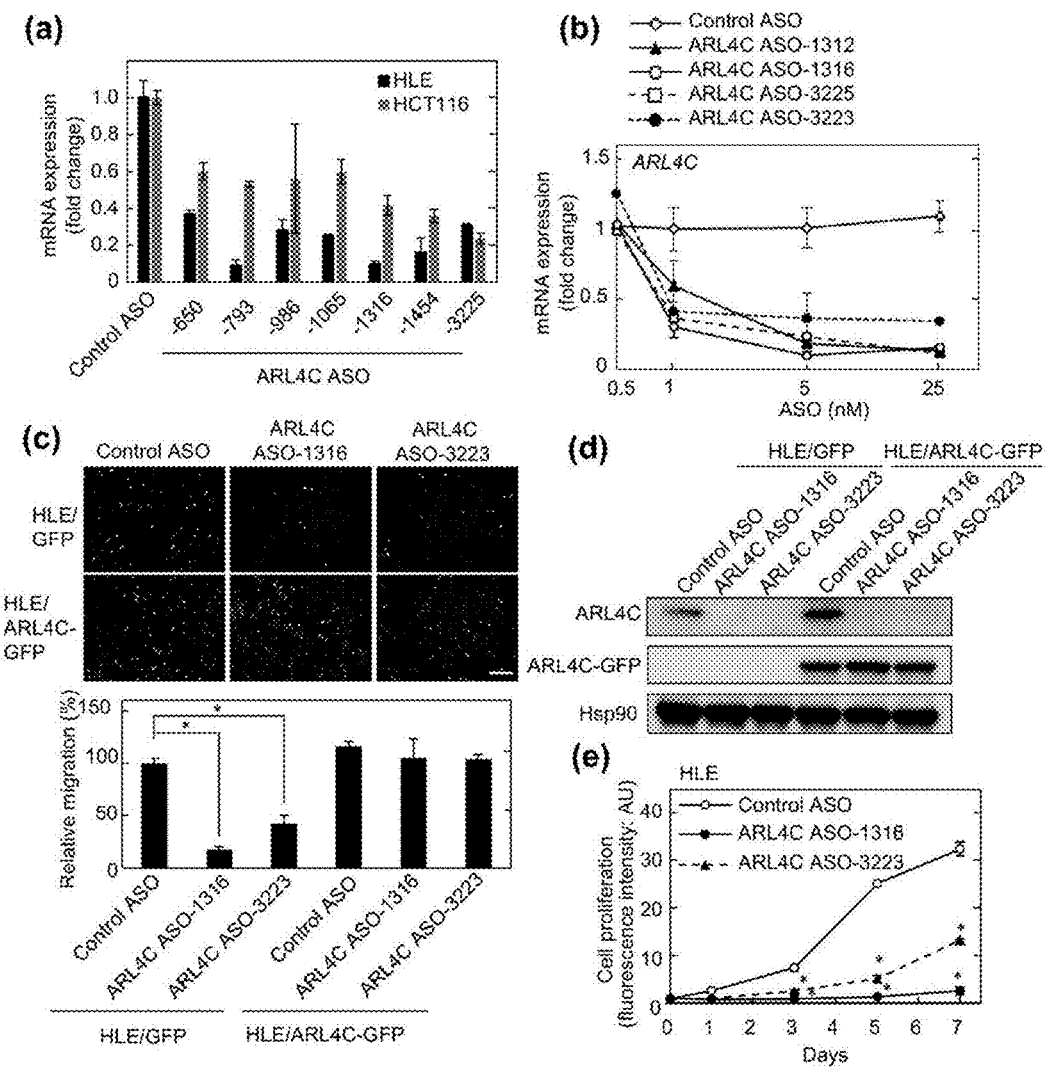
FIG. 4 (a) shows the results obtained by transfecting HLE cells and HCT116 cells with ARL4C ASOs (ASO-650, ASO-793, ASO-986, ASO-1065, ASO-1316, ASO-1454, and ASO-3225) at 25 nM each and measuring ARL4C mRNA amounts by real-time PCR. (b) shows the results obtained by transfecting HLE cells with ARL4C ASOs (ASO-1316, ASO-1312, ASO-3225, and ASO-3223) at 0.5 to 25 nM each and measuring ARL4C mRNA amounts by real-time PCR. (c) shows the results obtained by transfecting HLE/GFP cells or HLE/ARL4C-GFP cells with ASO-1316 and ASO-3223 at 25 nM and performing cell migration assay. (d) shows the results obtained by causing an anti-ARL4C antibody and an anti-Hsp90 antibody as probes to act on cell lysates of HLE/GFP cells and HLE/ARL4C-GFP cells transfected with ASO-1316 or ASO-3223. (e) shows the results obtained by transfecting HLE cells with control ASO, ASO-1316 and ASO-3223 at 25 nM and performing cell proliferation assay.

HLE cells and HCT116 cells were transfected with the above-described seven types of ARL4C ASOs and the control ASO at 25 nM, and the ARL4C mRNA amounts were measured by real-time PCR; the results thereof are shown in (a) of FIG. 4. As a result, it was confirmed that ASO-1316, ASO-1454 and ASO-3225 reduced the ARL4C mRNA amount in both of the HLE cells and the HCT116 cells. In order to optimize the effect of these three types of ARL4C ASOs, four bases were added to each of these three types of ARL4C ASOs, whereby ASO-1312, ASO-1450, and ASO-3223 each of which consisted of 19 bases were produced. With these six types of ARL4C ASOs (ASO-1316, ASO-1312, ASO-1454, ASO-1450, ASO-3225, and ASO-3223), the knockdown effect on ARL4C was further studied.

HLE cells were transfected with ARL4C ASOs (ASO-1316, ASO-1312, ASO-1454, ASO-1450, ASO-3225, and ASO-3223) at 25 nM each, and the ARL4C mRNA amounts were measured by real-time PCR; the results are shown in (c) of FIG. 3. In addition, HLE cells were transfected with ARL4C ASOs (ASO-1316, ASO-1312, ASO-3225, and ASO-3223) at 0.5 to 25 nM each, and the ARL4C mRNA amounts were measured by real-time PCR; the results are shown in (b) of FIG. 4. As a result, among the above-described six types of ARL4C ASOs, ASO-1316 and ASO-3223 were selected as ASOs having high effects of reducing the ARL4C mRNA amount in HLE cells at a low concentration.

Four genes of neurolysin (NLN), sapiens F-box and leucine-rich repeat protein 19 (FBXL19), keratin-associated protein 15-1 (KRTAP15-1), and sialic acid binding Ig-like lectin 6 (SIGLEC6) were identified as candidates for off-target genes of ASO-1316 and ASO-3223 by in silico analysis. HLE cells were transfected with ASO-1316 and ASO-3223 at 25 nM each, and mRNA amounts of NLN and FBXL19 were measured by real-time PCR; the results are shown in (d) of FIG. 3. The results show that ASO-1316 and ASO-3223 did not significantly affect the expression of NLN and FBXL19. In addition, KRTAP15-1 and SIGLEC6 were only slightly expressed in the HLE cells (data not shown). This suggests that an off-target effect that was suspected to be caused by the treatment of ASO-1316 and ASO-3223 did not occur.

HLE/GFP cells that stably express GFP or HLE/ARL4C-GFP cells that stably express ARL4C-GFP were transfected with control ASO, ASO-1316 and ASO-3223 at 25 nM, and a cell migration assay was carried out; the results of the assay are shown in (c) of FIG. 4. In addition, an anti-ARL4C antibody and an anti-Hsp90 antibody as probes were caused to act on cell lysates of the HLE/GFP cells or HLE/ARL4C-GFP cells transfected with ASO-1316 and ASO-3223 under the above-described conditions; the results are shown in (d) of FIG. 4. "Hsp90" represents a loading control. From these results, it was confirmed that both ASO-1316 and ASO-3223 suppress the migration of HLE cells caused by the overexpression of ARL4C.

HLE cells were transfected with control ASO, ASO-1316 and ASO-3223 at 25 nM and a proliferation assay was performed; the results of the assay are shown in (e) of FIG. 4. The results show that ASO-1316 and ASO-3223 inhibit HLE cells from proliferating.

In addition, HCT116 cells were transfected with control ASO, ASO-1316 and ASO-3223 at 25 nM, and a cell migration assay was carried out; the results are shown in (e) of FIG. 3. From these results, it was also confirmed that ASO-1316 and ASO-3223 suppress the migration of HCT116 cells.

The above-described results clarify that ASO-1316 and ASO-3223 are able to suppress the proliferation and migration of cancer cells expressing ARL4C.

2-3. Influences of ARL4C on PIK3CD in Liver Cancer Cells

It is known that Wnt/β-catenin signaling and EGF/Ras signaling stimulate the expression of ARL4C, which induces the nuclear localization of YAP/TAZ (EMBO J 2014; 33: 702-18, Oncogene 2015; 34: 4834-44).

Figure 5:
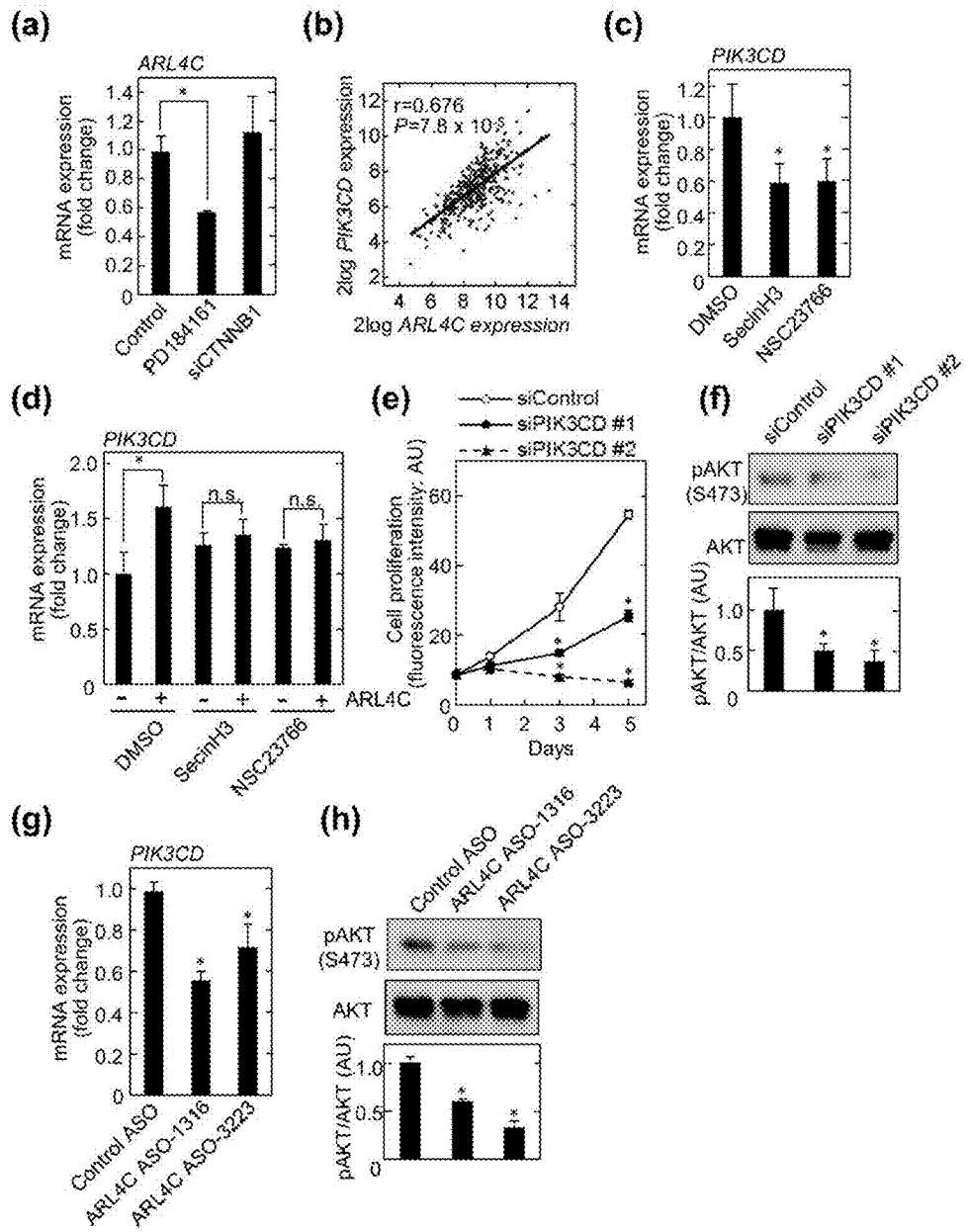
FIG. 5 (a) shows the results obtained by treating HLE cells with 10 µM PD184161 or 10 nM CTNNB1 siRNA and measuring ARL4C mRNA amounts by real-time PCR. (b) shows the results obtained by plotting of ARL4C mRNA amount (X-axis) and PIK3CD mRNA amount (Y-axis) in liver cancer using the TCGA data set using R2: Genomics Analysis and Visualization Platform. (c) shows the results obtained by treating HLE cells with 25 µM SecinH3 or 50 µM NSC23766 and measuring PIK3CD mRNA amounts by real-time PCR. (d) shows the results obtained by treating ARL4C-expressing HepG2 cells with 25 µM SecinH3 or 50 µM NSC23766 and measuring PIK3CD mRNA amounts by real-time PCR. (e) shows the results obtained by transfecting HLE cells with PIK3CD siRNA at 20 nM and performing cell proliferation assay. (f) shows the results obtained by causing an anti-phosphorylated AKT (pAKT S473) antibody and an anti-AKT antibody as probes to act on cell lysates of HLE cells transfected with PIK3CD siRNA. (g) shows the results obtained by transfecting HLE cells with ASO-1316 and ASO-3223 at 25 nM each and measuring PIK3CD mRNA amounts by real-time PCR. (h) shows the results obtained by causing an anti-phosphorylated AKT (pAKT S473) antibody and an anti-AKT antibody as probes to act on cell lysates of HLE cells transfected with ASO-1316 and ASO-3223.

HLE cells were treated with 10 µM PD184161 or 10 nM CTNNB1 siRNA (siRNA against CTNNB1), and the ARL4C mRNA amount was measured by real-time PCR; the results are shown in (a) of FIG. 5. In addition, HLE cells were treated with 10 nM CTNNB1 siRNA (siRNA against CTNNB1), and the ARL4C mRNA amount was measured by real-time PCR; the results thereof are shown in (a) of FIG. 6. PD184161 is a compound that inhibits MEK without knocking down 0-catenin. HLE cells treated with PD184161 had a reduced ARL4C mRNA amount, which suggests that ARL4C would act downstream of the MAPK pathway.

In addition, using the TCGA data set (n=371) using R2: Genomics Analysis and Visualization Platform, the ARL4C mRNA amount (X-axis), as well as the EGR1 mRNA amount, the FOS mRNA amount, the AXIN2 mRNA amount, the LGR5 mRNA amount (Y-axis) in liver cancer were plotted, and the result is shown in (b) of FIG. 6. This result shows that the mRNA amounts of EGR1 and FOS, which are the target genes of the MAPK pathway, positively correlate with the ARL4C mRNA amount, whereas the mRNA amounts of AXIN2 and the LGR5, which are the target genes of the Wnt/β-catenin signal, do not correlate with the ARL4C mRNA amount. In other words, the results of the analysis using this TCGA data set were in agreement with the results shown in (a) of FIG. 5 and (a) of FIG. 6.

Figure 6:
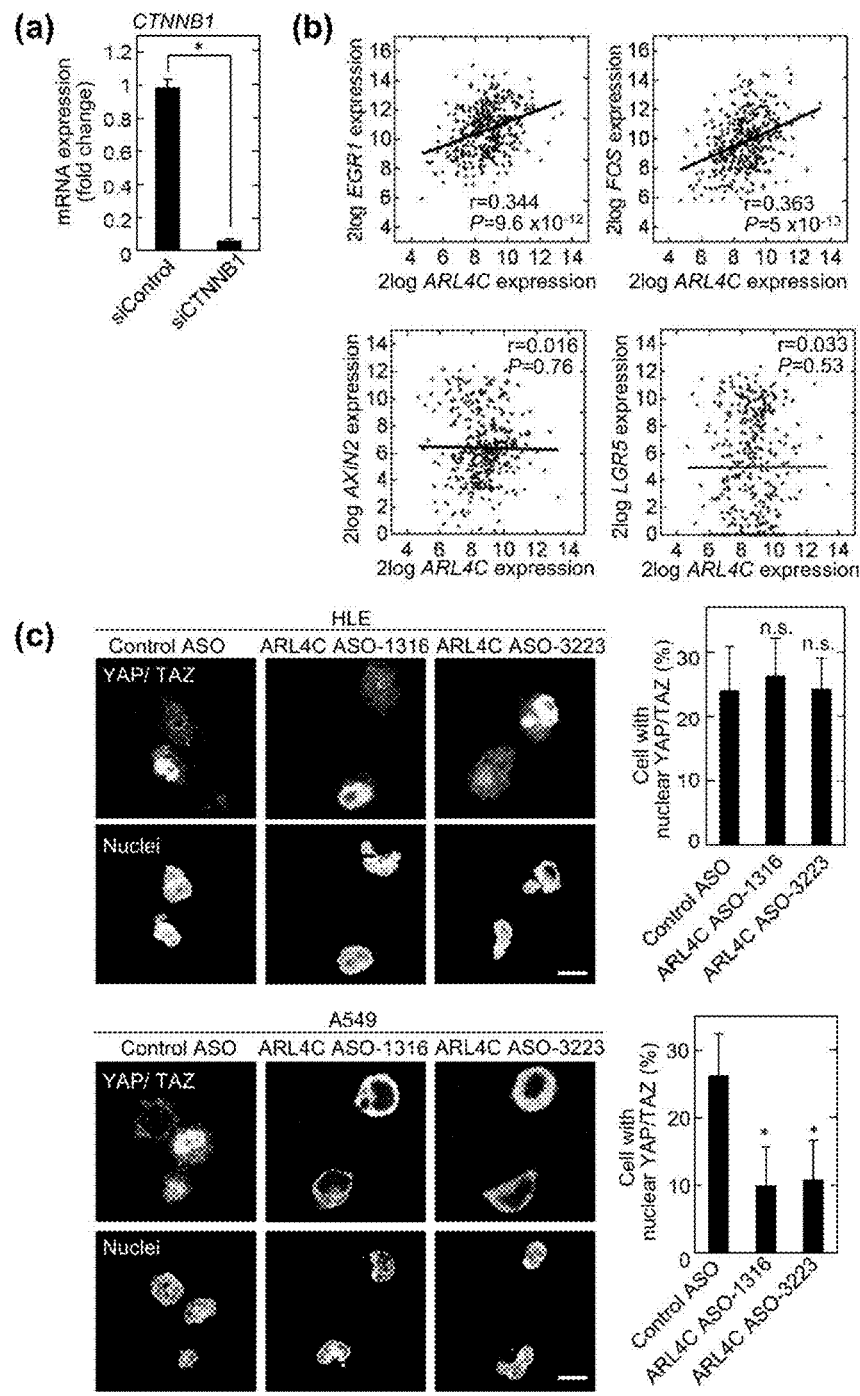
FIG. 6 (a) shows the results obtained by treating HLE cells with 10 nM CTNNB1 siRNA and measuring ARL4C mRNA amounts by real-time PCR. (b) shows the results obtained by plotting ARL4C mRNA amount (X-axis), EGR1 mRNA amount, FOS mRNA amount, AXIN2 mRNA amount, and LGR5 mRNA amount (Y-axis) in liver cancer using the TCGA dataset using R2: Genomics Analysis and Visualization Platform. (c) shows the results obtained by transfecting HLE cells or A549 cells with ASO-1316 and ASO-3223 at 25 nM and staining the same with an anti-YAP/TAZ antibody.

HLE cells or A549 cells were transfected with control ASO, ASO-1316, and ASO-3223 at 25 nM, and were stained with an anti-YAP/TAZ antibody; the results are shown in (c) of FIG. 6. As a result, it was confirmed that the knockdown of ARL4C in the A549 cells inhibited the nuclear localization of YAP, but the knockdown of ARL4C in the HLE cells did not affect the nuclear localization of YAP. Therefore, it was suggested that the genes expressed downstream of ARL4C and involved in the proliferation of cancer cells may differ between lung cancer cells and liver cancer cells.

Figure 7:
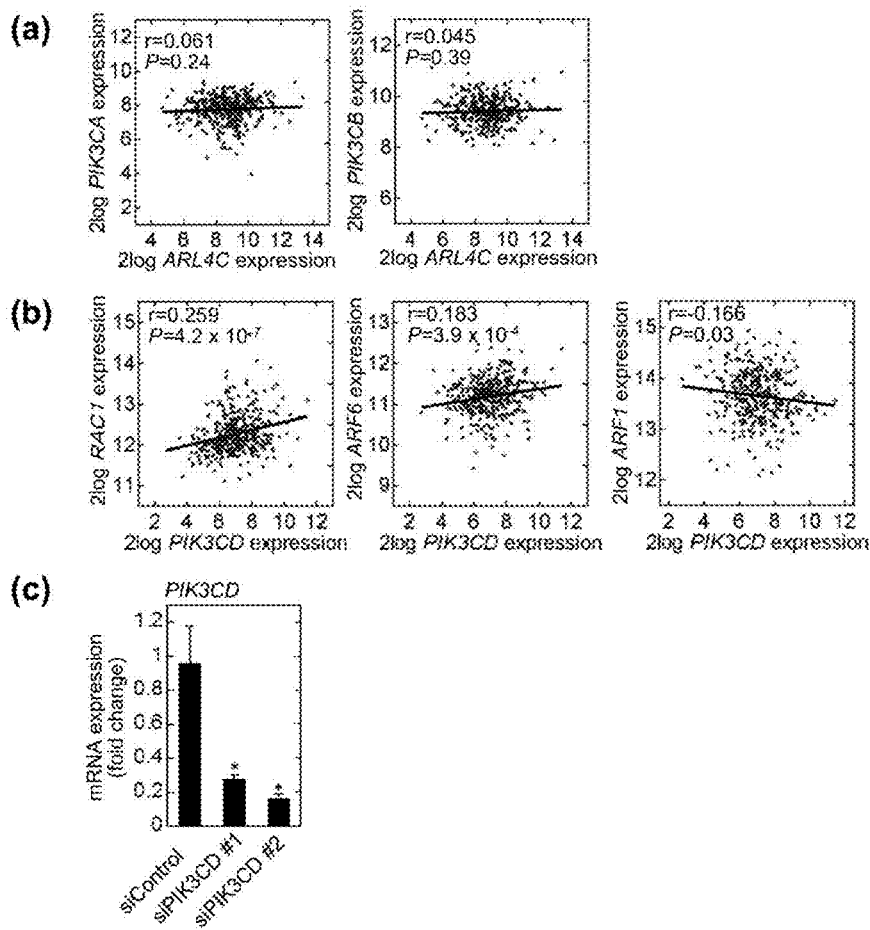
FIG. 7 (a) shows the results obtained by plotting ARL4C mRNA amount (X-axis) and mRNA amounts of PIK3CA and PIK3CB (Y-axis) using the TCGA dataset using R2: Genomics Analysis and Visualization Platform. (b) shows the results obtained by plotting ARL4C mRNA amount (X-axis), RAC1 mRNA amount, ARF6 mRNA amount, and ARF mRNA amount (Y-axis) using the TCGA data set. (c) shows the results obtained by transfecting HLE cells with PIK3CD siRNA at 20 nM and measuring PIK3CD mRNA amount by real-time PCR.

The phosphatidylinositol-3-kinase catalytic subunit 6 isoform (PIK3CD gene product) is known to be expressed in many cancers, including liver cancer (Blood 2010; 116: 1460-8, Hepatology). 2012; 55: 1852-62, Mol Cancer Ther 2008; 7: 841-50, Cancer Res 2003; 63: 1667-75). Therefore, using the TCGA dataset (n=371) using R2: Genomics Analysis and Visualization Platform, the correlation of the ARL4C mRNA amount with the PIK3CD mRNA amount, the PIK3CA mRNA amount, and the PIK3CB mRNA amount, in liver cancer was analyzed. The ARL4C mRNA amount (X-axis) and the PIK3CD mRNA amount (Y-axis) in liver cancer were plotted using the TCGA data set (n=371), and the result is shown in FIG. 5 (b). In addition, the ARL4C mRNA amount (X-axis), and the PIK3CA mRNA amount as well as the PIK3CB mRNA amount (Y-axis) in liver cancer were plotted using the TCGA data set (n=371), and the result is shown in (a) of FIG. 7. This result shows that in liver cancer, no correlation of the ARL4C mRNA amount with the amount of PIK3CA mRNA and the amount of PIK3CB mRNA was observed, but was positively correlated with the amount of PIK3CD mRNA.

HLE cells were treated with 25 µM SecinH3 (inhibitor of Arf nucleotide-binding site opener (ARNO)) or 50 µM NSC23766 (Rac inhibitor), and the amount of PIK3CD mRNA was measured by real-time PCR; the results are shown in (c) of FIG. 5. As a result, it was confirmed that the treatment with SecinH3 reduced the PIK3CD mRNA amount in the HLE cells. HepG2 cells expressing ARL4C (ARL4C-transduced HepG2 cells) were treated with 25 µM SecinH3 or 50 µM NSC23766, and the PIK3CD mRNA amount was measured by real-time PCR; the results thereof are shown in (d) of FIG. 4 Overexpression of ARL4C in the HepG2 cells increased the PIK3CD mRNA amount, but SecinH3 and NSC23766 suppressed an increase in the PIK3CD mRNA amount. In other words, this result suggests that ARL4C would upregulate the expression of PIK3CD via ARF6 and Rac.

In addition, using the TCGA dataset (n=371) using R2: Genomics Analysis and Visualization Platform, the ARL4C mRNA amount (X-axis), and the RAC1 mRNA amount, the ARF6 mRNA amount, as well as the ARF mRNA amount (Y-axis) in liver cancer were plotted, and the result is shown in (b) of FIG. 7. This result shows that in liver cancer, no correlation of the ARL4C mRNA amount with the ARF mRNA amount was observed, but the ARL4C mRNA amount was positively correlated with the mRNA amounts of ARF6 and RAC1. In other words, the results of the analysis using this TCGA data set were in agreement with the results shown in (c) and (d) of FIG. 5.

HLE cells were transfected with control siRNA and PIK3CD siRNA (siRNA against PIK3CD) at 20 nM, and a proliferation assay was performed; the results are shown in (e) of FIG. 5. In addition, an anti-phosphorylated AKT antibody and an anti-AKT antibody as probes were caused to act on cell lysates of HLE cells transfected with control siRNA and PIK3CD siRNA; the results are shown in FIG. 5 (f). HLE cells were transfected with control siRNA and PIK3CD siRNA (siRNA against PIK3CD) at 20 nM and the PIK3CD mRNA amount was measured by real-time PCR; the results are shown in (c) of FIG. 7. From these results, it was clarified that the knockdown of PIK3CD in the HLE cells suppressed cell proliferation and reduced AKT activity.

HLE cells were transfected with control ASO, ASO-1316, and ASO-3223 at 25 nM, and the PIK3CD mRNA amount was measured by real-time PCR; the results are shown in (g) of FIG. 5. In addition, an anti-phosphorylated AKT (pAKT S473) antibody and an anti-AKT antibody as probes were caused to act on cell lysates of HLE cells transfected with control ASO, ASO-1316, and ASO-3223; the results are shown in (h) of FIG. 5. These results suggest that PIK3CD was a downstream target molecule of ARL4C in cancer cells, and that ASO-1316 and ASO-3223, suppressing PIK3CD expression, could inhibit cancer cells from proliferating.

2-4. Examination of Antitumor Effect of ARL4C ASO in Primary Liver Tumor Model

In a primary liver tumor model in which HLE cells were directly transplanted into the liver, influences of the subcutaneous administration of ARL4C ASO (ASO-1316 and ASO-3223) on liver tumors was examined.

In experiments in the primary liver tumor model, Matrigel containing HEL cells at a high concentration was injected into the liver of a mouse (day 0), and control ASO, ASO-1316, and ASO-3223 were subcutaneously administered on and after day 0, at a frequency of twice a week. The tumor formed in the liver was observed when 29 days had elapsed since the transplantation; the result is shown in (a) of FIG. 8. In addition, when 29 days had elapsed since the transplantation, the tumor formed in the liver was immunostained with an anti-ARL4C antibody and an anti-PIK3CD antibody, the result of which is shown in (b) of FIG. 8, and the tumor was immunostained with an anti-Ki-67 antibody, the result of which is shown in (c) of FIG. 8. As a result, it was confirmed that ASO-1316 was able to suppress the HLE tumorigenesis and was able to reduce the tumor size by half as compared with the control ASO. It was also confirmed that ASO-1316 was able to suppress the expression of ARL4C and PIK3CD in tumors formed in the liver and was able to reduce the number of Ki-67-positive cells. ASO-1316 did not induce histological damage or cell death in the non-tumor area of the liver. On the other hand, ASO-3223 had almost no influence on HLE tumorigenesis, the expression of ARL4C and PIK3CD, and the number of Ki-67-positive cells, and no antitumor effect was observed in vivo.

Figure 9:
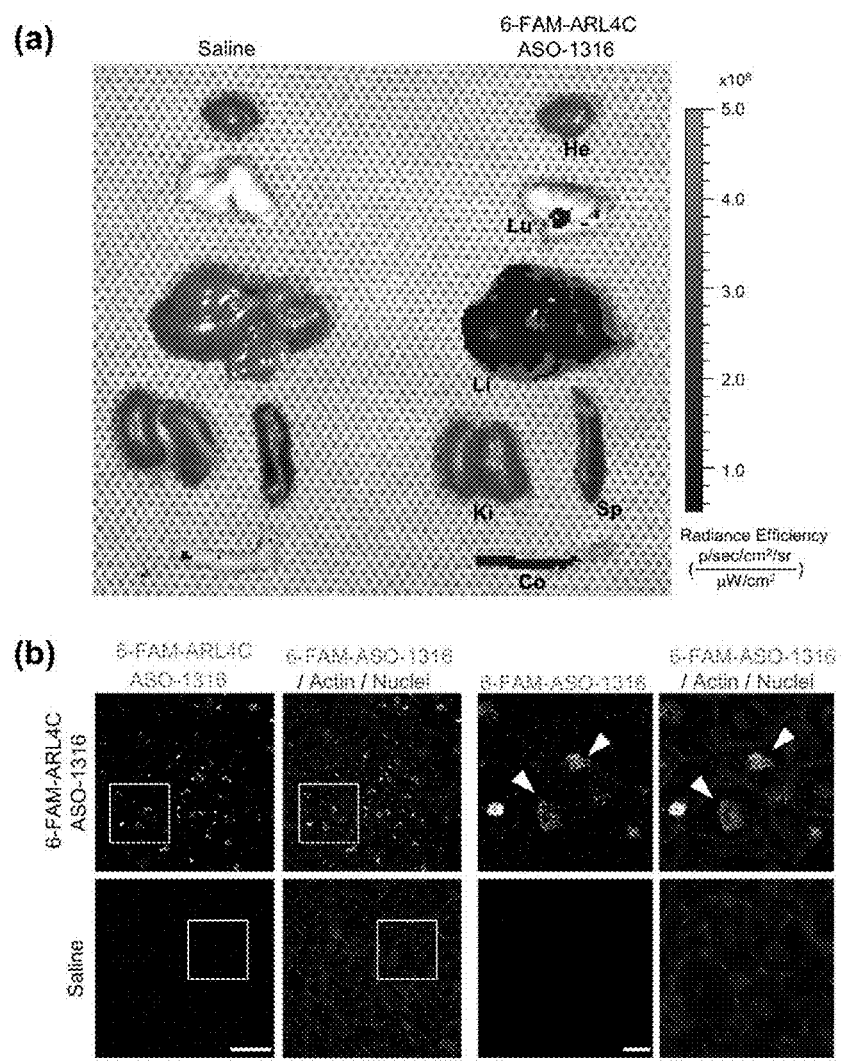
FIG. 9 (a) shows the results obtained by subcutaneously administering 6-FAM-labeled ASO-1316 to a normal mouse to which HCT116 cells had not been transplanted, and measuring fluorescence intensities in various organs 4 hours after. (b) shows the results obtained by subcutaneously administering 6-FAM-labeled ASO-1316 to normal mice in which HCT116 cells had not been transplanted, and staining liver specimens obtained 4 hours after, with phalloidin (F-actin) and Hoechst 33342 (nucleus).

In addition, 6-FAM-labeled ASO-1316 or buffer (Saline) was subcutaneously administered to normal mice to which HLE cells had not been transplanted, and fluorescence intensities in various organs were measured four hours after that; the results are shown in (a) of FIG. 9. In addition, 6-FAM-labeled ASO-1316 or buffer (Saline) was subcutaneously administered to normal mice to which HLE cells had not been transplanted, and liver specimens obtained 4 hours after that were stained with phalloidin and Hoechst 33342 so that the locations of F-actin and the nuclei were indicated; the results are shown in (b) of FIG. 9. These results show that ASO-1316, which was subcutaneously administered to normal mice, was specifically delivered to the liver, but the uptake of the same was small.

Figure 8:
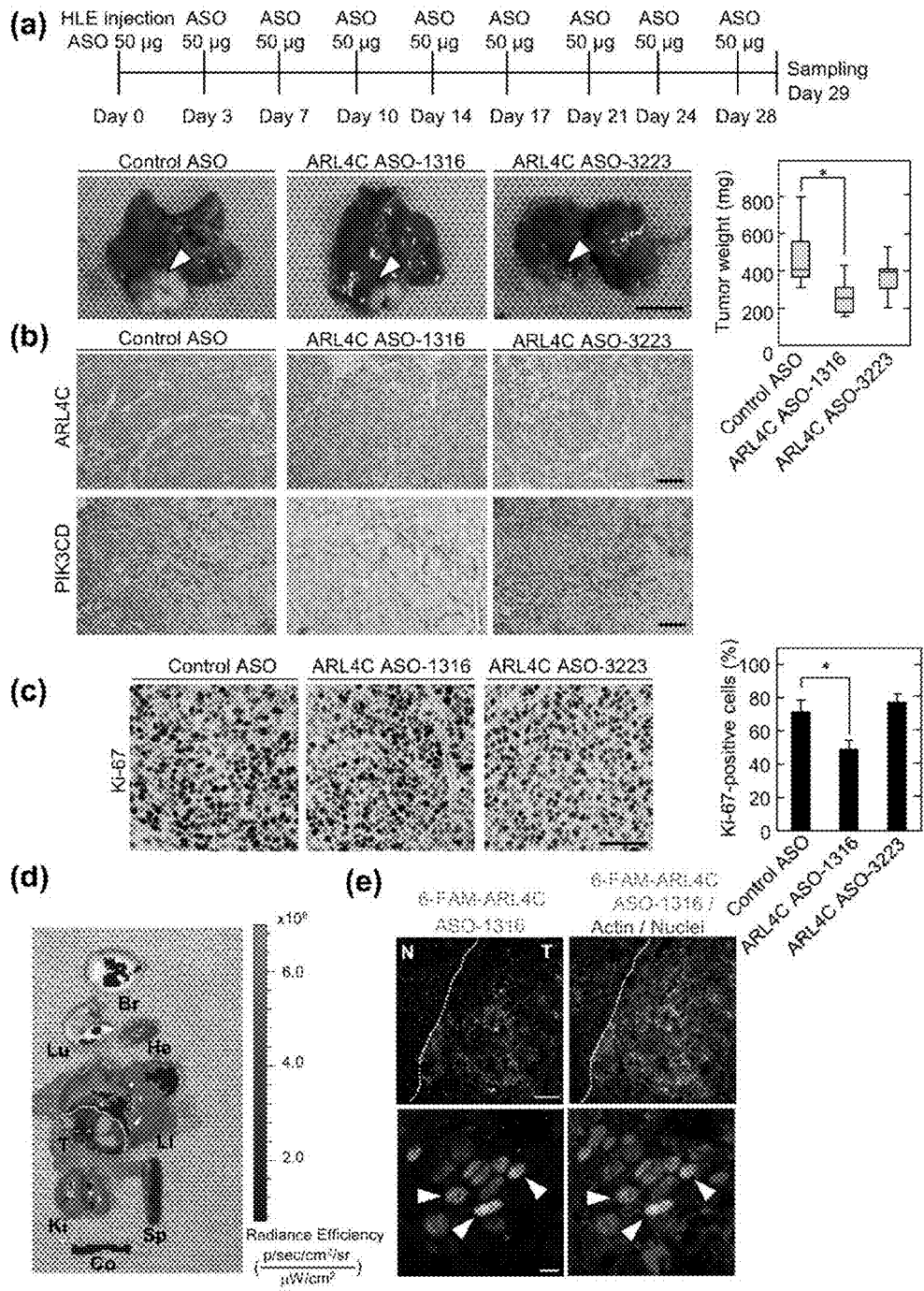
FIG. 8 shows the results obtained by examining antitumor effects of ARL4C ASOs using a primary liver tumor model. (a) shows the results obtained by observing tumors formed in the livers 29 days after the transplantation of HLE cells. (b) shows the results obtained by immunostaining tumors formed in the livers 29 days after the transplantation, with an anti-ARL4C antibody and an anti-PIK3CD antibody. (c) shows the results obtained by immunostaining tumors formed in the livers 29 days after the transplantation, with an anti-Ki-67 antibody. (d) shows the results obtained by administering 6-FAM-labeled ASO-1316 to a mouse cancer model transplanted with HLE cells and measuring respective fluorescence intensities in various organs 4 hours after. (e) is the result obtained by administering 6-FAM-labeled ASO-1316 to a mouse cancer model transplanted with HLE cells, and staining liver specimens obtained 4 hours after with phalloidin (F-actin) and Hoechst 33342 (nucleus).

6-FAM-labeled ASO-1316 or buffer (Saline) was subcutaneously administered to a mouse primary liver tumor model transplanted with HLE cells, and fluorescence intensities in various organs were measured four hours after that; the results are shown in (d) of FIG. 8. In addition, 6-FAM-labeled ASO-1316 was administered to a mouse cancer model transplanted with HLE cells, and liver specimens obtained four hours after that were stained with phalloidin and Hoechst 33342 so that the locations of F-actin and the nuclei were indicated; the results are shown in (e) of FIG. 8. From these results, it was confirmed that when ASO-1316 was subcutaneously administered to a mouse cancer model, the ASO was efficiently accumulated in the tumor area of the liver and was accumulated in the nuclei of the tumor cells.

In addition, since ASO-1312 has a base sequence that overlaps with that of ASO-1316, it can be highly expected that an antitumor effect will be exerted in the primary liver tumor model, as is the case with ASO-1316.

2-5. Examination of Antitumor Effect of ARL4C ASO in Metastatic Tumor Model

In a metastatic tumor model in which HCT116 cells were transplanted into the spleen and the tumor was caused to metastasize to the liver, influences of the subcutaneous administration of ARL4C ASO (ASO-1316 and ASO-3223) on the liver tumor was examined.

Figure 10:
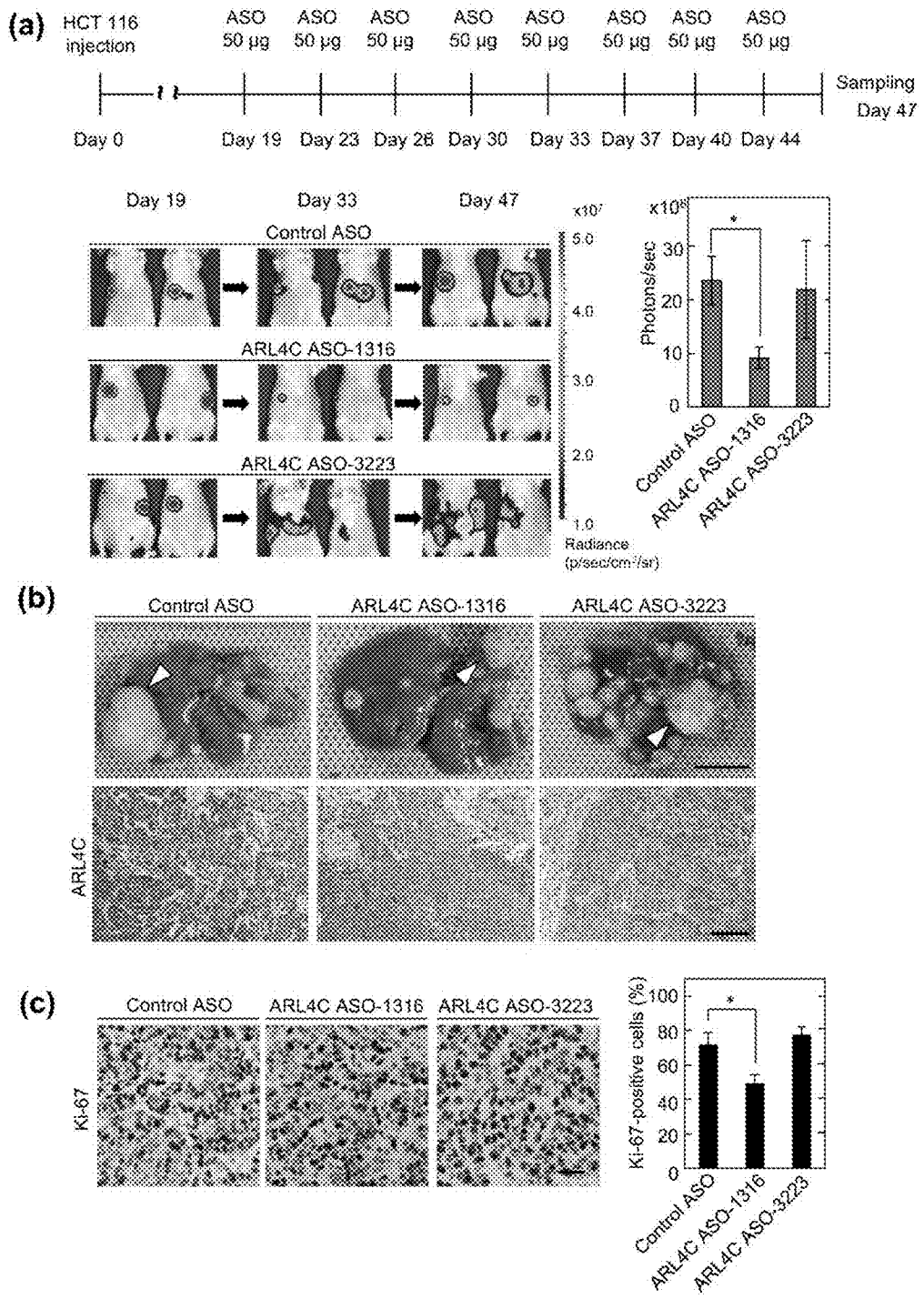
FIG. 10 shows the results obtained by examining an antitumor effect of ARL4C ASO using a metastatic tumor model. (a) shows the results obtained by observing fluorescence of luciferase emitted from a liver tumor on days 19, 35 and 47, and the results obtained by quantifying luminescence intensities of luciferase emitted from a liver tumor on day 47. (b) shows the results obtained by observing the tumors formed in the livers when 47 days had elapsed since the transplantation to the spleens, and the results obtained by immunostaining the tumors formed in the livers with an anti-ARL4C antibody when 47 days had elapsed since the transplantation. (c) shows the results obtained by immunostaining tumors formed in the livers with an anti-Ki-67 antibody when 47 days had elapsed since the transplantation.

In an experiment in the metastatic tumor model, HCT116/Luc cells were injected into the spleens (day 0), luciferase signals were detected in the livers 19 days after the injection; on and after this day, control ASO, ASO-1316, and ASO-3223 were subcutaneously administered at a frequency of twice a week. When 19, 35 and 47 days had elapsed, the fluorescence of luciferase emitted from the liver tumors was observed, and when 47 days had elapsed, fluorescence intensities of luciferase emitted from the liver tumors were quantified with software of IVIS/Kodak; the results are shown in (a) of FIG. 10. In the case where ASO-1316 was administered, in the liver tumors that were confirmed to have been engrafted 19 days after the injection of HCT116/Luc cells, the growth of the tumors until 47 days after the injection could be suppressed. In addition, when 47 days had elapsed since the transplantation of HCT116/Luc cells, the tumors formed in the livers were observed, and the tumors formed in the livers were immunostained with an anti-ARL4C antibody; the results are shown in (b) of FIG. 10. The tumors formed in the livers were immunostained with an anti-Ki-67 antibody when 47 days had elapsed since the transplantation of HCT116/Luc cells; the results are shown in (c) of FIG. 10. From these results, it was also confirmed that the liver tumor of mouse treated with ASO-1316 had decreased ARL4C expression levels and decreased numbers of Ki-67 positive cells.

On the other hand, ASO-3223 did not exert an antitumor effect in the metastatic tumor model, as is the case with the result of the primary liver tumor model.

In addition, since ASO-1312 has a base sequence that overlaps with that of ASO-1316, it can be highly expected that an antitumor effect will be exerted in the metastatic tumor model, as is the case with ASO-1316.

2-6. Examination of Antitumor Effect of ARL4C ASO in Lung Cancer Tumor Model Influences of ARL4C ASO (ASO-1316) on tumors was examined in a xenograft orthotopic transplantation model in which A549/Luc cells were transplanted into the lung.

Figure 11:
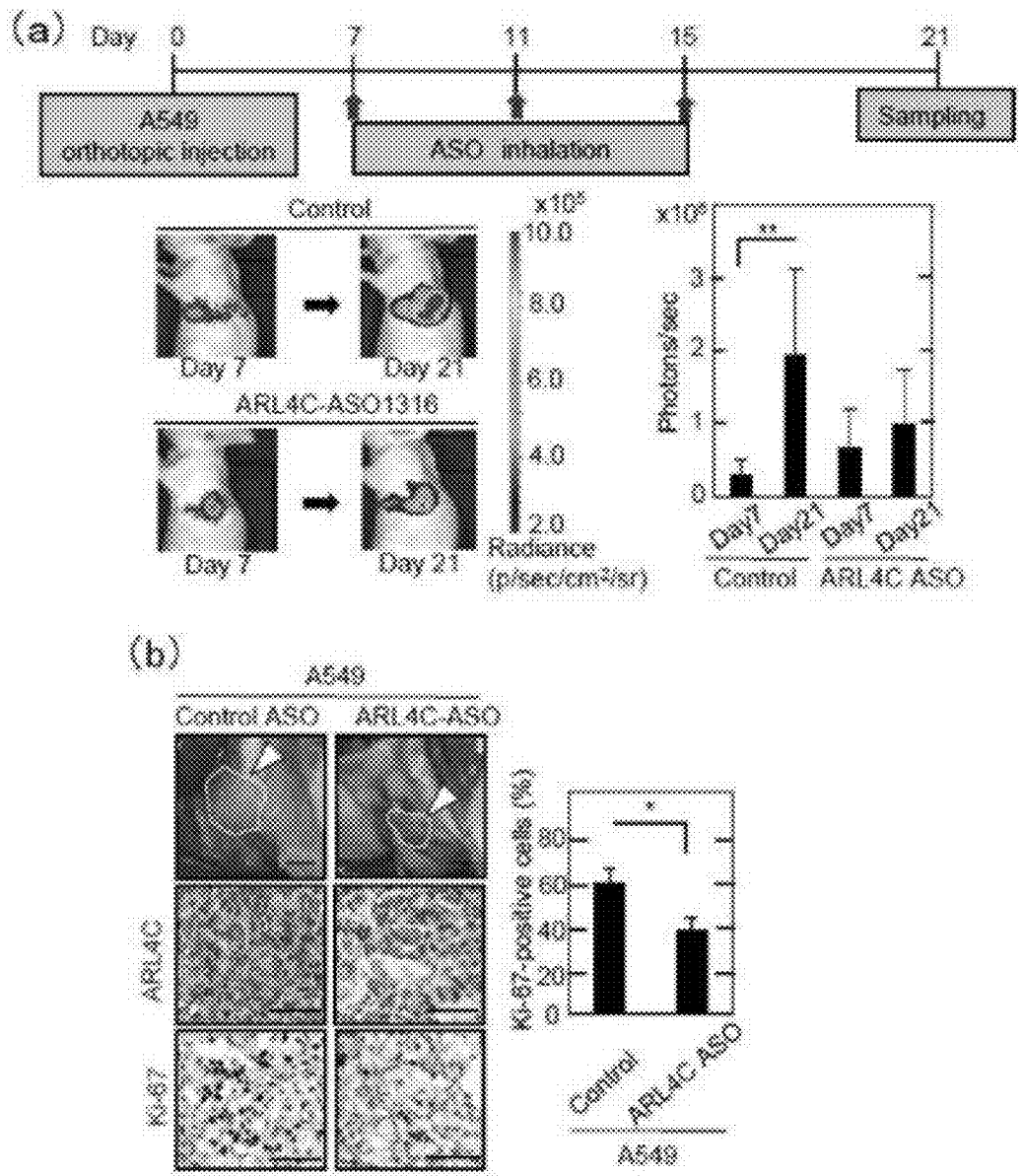
FIG. 11 shows the results obtained by examining an antitumor effect of ARL4C ASO in a xenograft orthotopic transplantation model using lung cancer cells. The left part of (a) shows bioluminescent images of the left lungs observed 7 and 21 days after the transplantation, and the right part of (a) shows the results obtained by measuring luminescence intensities of luciferase emitted from the tumors of the left lungs. The upper left part of (b) shows representative images of the left lungs transplanted with A549/Luc cells 21 days after the transplantation; the middle left part of (b) shows the results obtained by preparing sections from tumors in the left lungs and immunostaining the same with an anti-ARL4C antibody; and the lower left part of (b) shows the results obtaining by preparing sections from the left lungs and immunostaining the same with an anti-Ki-67 antibody. The right part of (b) shows the results obtained by preparing sections from tumors in the left lungs, immunostaining the same with an anti-Ki-67 antibody, and counting Ki-67-positive cells.

In an experiment in a xenograft orthotopic transplantation model using lung cancer cells, A549/Luc cells were transplanted into the left lung (day 0), and transbronchial administration of control ASO and ARL4C ASO-1316 was carried out when 7, 11 and 15 days had elapsed after the transplantation. Bioluminescent images of the left lung observed 7 and 21 days after the transplantation of A549/Luc cells are shown in the left part of (a) of FIG. 11. In addition, when 7 and 21 days had elapsed since the transplantation, luminescence intensities of luciferase emitted from tumors in the left lungs in the mice were measured using software of IVIS/Kodak; the results are shown in the right part of (a) of FIG. 11. From these results, it was confirmed that ARL4C ASO-1316 inhibited A549/Luc cells from proliferating. In addition, representative images of the left lungs transplanted with A549/Luc cells, which were taken when 21 days had elapsed since the transplantation, are shown in the upper left part of (b) of FIG. 11. In the images in the upper left part of (b) of FIG. 11, each white arrow indicates the location of the tumor, and each dotted line indicates the outline of the tumor. The images in the left middle part of (b) of FIG. 11 show the results obtained by preparing sections from the tumors in the left lungs and immunostaining the same with an anti-ARL4C antibody, and the images in the lower left part of (b) of FIG. 11 show the results obtained by preparing sections from the tumors in the left lungs and immunostaining the same with an anti-Ki-67 antibody. In addition, the right part of (b) in FIG. 11 shows the results obtained by preparing sections from the tumors in the left lungs, immunostaining the same with the anti-Ki-67 antibody, and counting Ki-67 positive cells (mean t standard deviation). From the results shown in (b) of FIG. 11 as well, it was confirmed that the mouse to which ASO-1316 was administered had decreased expression of ARL4C and Ki-67-positive cells decreased in number.

2-7. Examination of Metastasis Inhibitory Effect and Antitumor Effect of ARL4C ASO in Pancreatic Cancer Tumor Model Influences of ARL4C ASO (ASO-1316) on tumorigenesis and mesenteric lymph node (mLN) metastasis were examined in a xenograft orthotopic transplantation model in which S2-CP8/Luc cells were transplanted into the lung.

Figure 12:
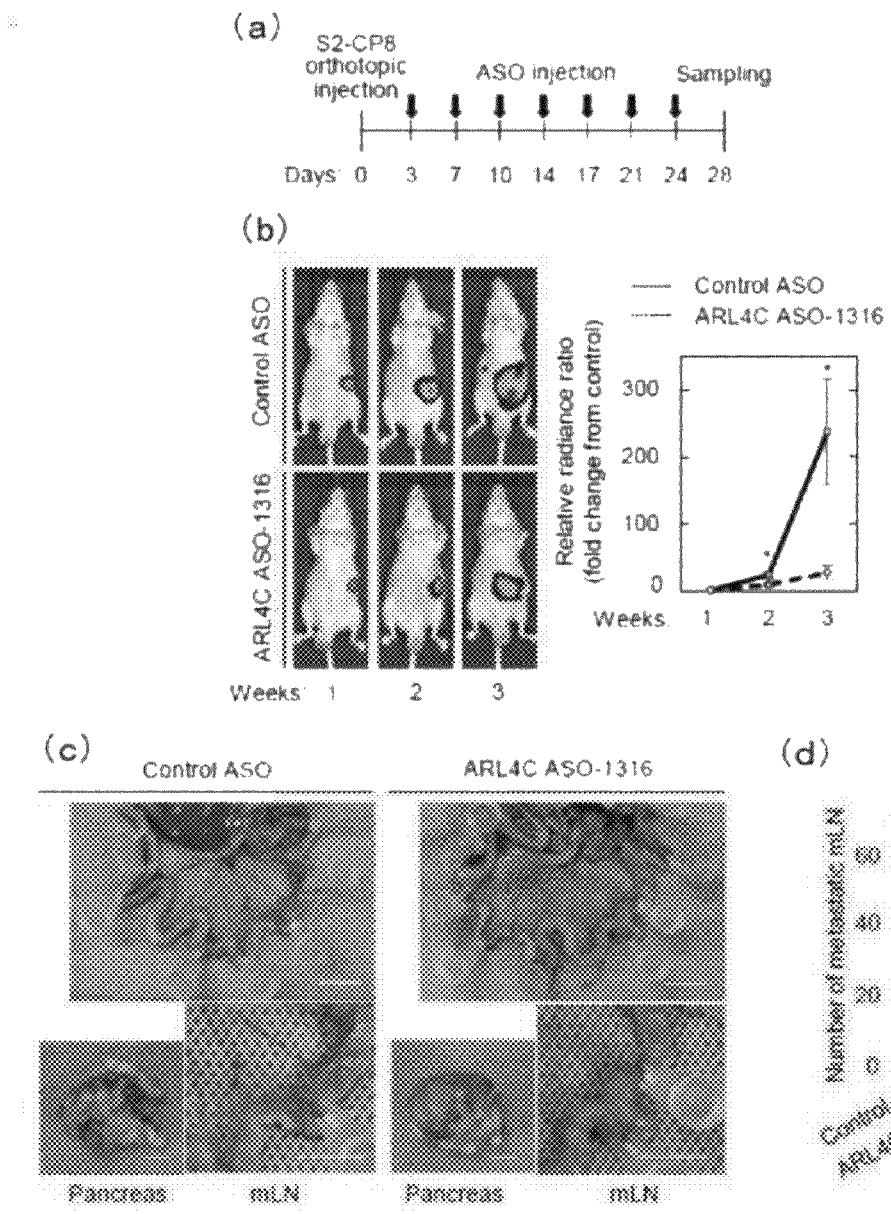
FIG. 12 shows the results obtained by examining the tumor metastasis inhibitory effect and antitumor effect of ARL4C ASO in a xenograft orthotopic transplantation model using pancreatic cancer cells. (a) shows the test conditions in a xenograft orthotopic transplantation model using pancreatic cancer cells. The left part of (b) shows bioluminescent images of intraperitoneal tumors observed 7, 14 and 21 days after the transplantation of pancreatic cancer cells, and the right part of (b) shows the results obtained by quantifying, by radiance, the intraperitoneal tumors in the abdominal cavities of mice 7 days after the transplantation. (c) shows representative images of tumors found in the excised pancreas and mesenteric lymph nodes 28 days after the transplantation of pancreatic cancer cells. (d) shows the results obtained by counting the number of mesenteric lymph nodes 28 days after the transplantation of pancreatic cancer cells.

In an experiment in a xenograft orthotopic transplantation model using pancreatic cancer cells, S2-CP8/Luc cells were transplanted into the pancreas (day 0), and control ASO and ASO-1316 were intraperitoneally administered on and after 3 days after the transplantation, twice a week. Bioluminescent images of intraperitoneal tumors observed when 7, 14, and 21 days had elapsed after the transplantation of S2-CP8/Luc cells are shown in the left part of (b) of FIG. 12. The intraperitoneal tumors in the abdominal cavities of mice 7 days after the transplantation were quantified by radiance; the results are shown in the right part of (b) of FIG. 12. Representative images of the tumors found in the pancreas and the mesenteric lymph nodes that were excised 28 days after the transplantation are shown in (c) of FIG. 12. The numbers of the tumors found in the mesenteric lymph nodes were counted 28 days after the transplantation; the results are shown in FIG. 12 (*d*). In (d) of FIG. 12, the number of mesenteric lymph nodes shows the mean t standard deviation, and * indicates that P<0.05. From these results, it was confirmed that ASO-1316 could suppress cancer metastasis to mesenteric lymph nodes.

The invention claimed is:

1. An antisense oligonucleotide targeting ARL4C, consisting of a base sequence of:
   (i) a sequence represented by SEQ ID NO: 1, or
   (ii) a sequence consisting of the sequence represented by SEQ ID NO: 1 and 1-35 additional bases that are not represented by SEQ ID NO: 1 but that are adjacent to the 5' and/or the 3' side of the sequence of SEQ ID NO: 1 in the sequence complementary to the sequence of SEQ ID NO: 3, wherein the number of bases of the antisense oligonucleotide is from 16 to 50,
   wherein the antisense oligonucleotides of (i) and (ii) have at least one chemically modified nucleotide shown in (1) to (3):
   (1) a nucleotide having a substituent in the base moiety, wherein the substituent is a linear alkyl group having 1 to 6 carbon atoms, a linear alkoxy group having 1 to 6 carbon atoms, a mercapto group, a linear alkylthio group having 1 to 6 carbon atoms, an amino group, a linear alkylamino group having 1 to 6 carbon atoms, or a halogen atom,
   (2) a nucleotide having a chemically modified sugar moiety, wherein the nucleotide is a 2',4'-bridged nucleotide or a nucleotide in which the hydroxyl group at the 2' position of the sugar moiety is substituted with an alkoxy group or with a halogen atom,
   (3) a nucleotide having a chemically modified internucleoside bond, wherein the chemically modified internucleoside bond is least one member selected form the group consisting of phosphorothioate, chiral phosphorothioate, phosphorodithioate, phosphotriester, aminoalkylphosphotriester, 3'-alkylene phosphonate, 5'-alkylene phosphonate, phosphinate, 3'-aminophosphoramidate, aminoalkylphosphoramidate, thionophosphoramidate, thionoalkylphosphonate, thionoalkylphosphotriester, selenophosphate, and boranophosphate.

2. The antisense oligonucleotide according to claim 1, consisting of the base sequence represented by SEQ ID NO: 2.

3. The antisense oligonucleotide according to claim 1, wherein at least one nucleotide is a 2',4'-bridged nucleotide.

4. The antisense oligonucleotide according to claim 1, wherein the 2',4'-bridged nucleotide has a structure shown in General Formula (1) below:

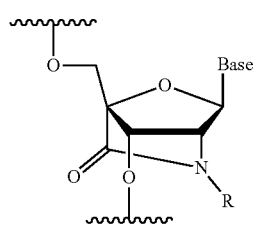

(1)

where "Base" represents a purine-9-yl group or a 2-oxo-1,2-dihydropyrimidine-1-yl group which may be substituted with a substituent, and "R" represents a hydrogen atom; an alkyl group having 1 to 7 carbon atoms wherein the alkyl group may be branched or may form a ring; an alkenyl group having 2 to 7 carbon atoms wherein the alkenyl group may be branched or may form a ring; an aryl group having 3 to 12 carbon atoms wherein the aryl group may have a substituent and may include a heteroatom; or an aralkyl group having an aryl moiety having 3 to 12 carbon atoms wherein the aryl moiety may have a substituent and may include a heteroatom.

5. The antisense oligonucleotide according to claim 1, wherein at least one of the internucleoside bonds is a phosphorothioate bond.

6. The antisense oligonucleotide according to claim 1, wherein all of the internucleoside bonds are phosphorothioate bonds, and the 1st to 3rd nucleotides from the 5'-terminal and the 2nd and 3rd nucleotides from the 3'-terminal are 2',4'-bridged nucleotides.

7. The antisense oligonucleotide according to claim 1, wherein the antisense oligonucleotide is a chemically modified antisense oligonucleotide consisting of Sequence A or Sequence B shown below:
Sequence A: G(Y)^5(Y)^A(Y)^t^a^c^c^t^c^a^g^g^T(Y)^A(Y)^a SEQ ID NO: 104);
Sequence B: G(Y)^5(Y)^A(Y)^t^a^c^c^t^c^a^g^g^t^a^a^t^T(Y)^5(Y)^a (SEQ ID NO: 105)
where "G(Y)" represents guanine having a structure of AmNA (2',4'-bridged nucleotide in which R is a methyl group in General Formula (1) described above),
"A(Y)" represents adenine having a structure of AmNA,
"T(Y)" represents thymine having a structure of AmNA,
"5(Y)" represents 5-methylcytosine having a structure of AmNA, and
"^" represents a phosphorothioate bond.

8. A nucleic acid drug comprising the antisense oligonucleotide according to claim 1.

9. A method of treating a liver cancer, a colorectal cancer, a lung cancer, or a tongue cancer in a subject comprising administering the nucleic acid drug according to claim 8 to the subject.

10. A method of treating a metastatic liver cancer, or a cancer metastatic from a pancreatic cancer in a subject comprising administering the nucleic acid drug according to claim 8 to the subject.

11. A method of manufacturing an antitumor agent comprising obtaining the antisense oligonucleotide according to claim 1.

12. A method for treating a tumor, comprising administering, to a tumor patient, a therapeutically effective amount of an antisense oligonucleotide, wherein the antisense oligonucleotide targeting ARL4C is consisting of a base sequence of:
(i) a sequence represented by SEQ ID NO: 1, or
(ii) a sequence consisting of the sequence represented by SEQ ID NO: 1 and 1-35 additional bases that are not represented by SEQ ID NO: 1 but that are adjacent to the 5' and/or the 3' side of the sequence of SEQ ID NO: 1 in the sequence complementary to the sequence of SEQ ID NO: 3, wherein the number of bases of the antisense oligonucleotide is from 16 to 50, and
wherein the tumor patient has a cancer selected from the group consisting of liver cancer, colorectal cancer, lung cancer, tongue cancer and pancreatic cancer.

13. The method according to claim 12, wherein the antisense oligonucleotide targeting ARL4C has the sequence of SEQ ID NO: 2.

* * * * *